US012329216B2

(12) United States Patent
Masna et al.

(10) Patent No.: US 12,329,216 B2
(45) Date of Patent: Jun. 17, 2025

(54) SYSTEM AND METHOD FOR CLOSED-LOOP ACTIVE SENSING AND PROTECTION AGAINST AIRBORNE PATHOGENS

(71) Applicant: University of Florida Research Foundation, Inc., Gainesville, FL (US)

(72) Inventors: Naren Vikram Raj Masna, Gainesville, FL (US); Swarup Bhunia, Gainesville, FL (US); Soumyajit Mandal, Gainesville, FL (US); Anamika Bhuniaroy, Gainesville, FL (US); Rohan Reddy Kalavakonda, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 917 days.

(21) Appl. No.: 17/369,283

(22) Filed: Jul. 7, 2021

(65) Prior Publication Data

US 2022/0007763 A1  Jan. 13, 2022

Related U.S. Application Data

(60) Provisional application No. 63/049,798, filed on Jul. 9, 2020.

(51) Int. Cl.
*A41D 13/11* (2006.01)
*A61B 5/00* (2006.01)
(Continued)

(52) U.S. Cl.
CPC ........ *A41D 13/1192* (2013.01); *A61B 5/0082* (2013.01); *A61B 5/082* (2013.01);
(Continued)

(58) Field of Classification Search
CPC ........... A41D 13/11–1192; A61L 9/015; A61L 9/14–145; A61L 9/18–20;
(Continued)

(56) References Cited

U.S. PATENT DOCUMENTS

2021/0310928 A1*  10/2021  Huang ............... G01N 15/0656
2021/0353785 A1*  11/2021  Bonutti ..................... A23L 3/28
(Continued)

FOREIGN PATENT DOCUMENTS

AU        2020100503 A4  *  5/2020
CN         105771107 A  *  7/2016
(Continued)

OTHER PUBLICATIONS

Translation of CN 108375530. Accessed from PE2E-Search on Apr. 29, 2024. (Year: 2018).*
(Continued)

*Primary Examiner* — Valerie L Woodward
*Assistant Examiner* — Paige Kathleen Bugg
(74) *Attorney, Agent, or Firm* — Thomas | Horstemeyer, LLP

(57) ABSTRACT

A mask apparatus that is configured to prevent airborne pathogens from reaching an individual by actively mitigating airborne droplets that have a pathogen. In one example, the mask apparatus comprises a sensor device, a mitigator device, and a controller. The sensor device comprises an aerosol detector that is configured to perform a light measurement of an airborne aerosol droplet in an area proximate to the wearable apparatus. The mitigator device is configured to initiate a mitigation action directed at the airborne aerosol droplet. The controller is data communication with the sensor device and the mitigator device. The controller is configured to determine that the airborne aerosol droplet has a pathogen based at least in part on the light measurement
(Continued)

captured by the sensor device and cause the mitigator device to initiate the mitigation action based on the airborne aerosol droplet having the pathogen.

20 Claims, 25 Drawing Sheets

(51) Int. Cl.
*A61B 5/08* (2006.01)
*A61B 5/097* (2006.01)
*A61L 9/14* (2006.01)
*A61L 9/20* (2006.01)

(52) U.S. Cl.
CPC ............ *A61B 5/097* (2013.01); *A61B 5/4836* (2013.01); *A61B 5/6803* (2013.01); *A61B 5/7267* (2013.01); *A61L 9/14* (2013.01); *A61L 9/20* (2013.01); *A61B 2562/0233* (2013.01); *A61B 2562/0271* (2013.01); *A61B 2562/029* (2013.01); *A61L 2209/111* (2013.01)

(58) Field of Classification Search
CPC ...... A62B 18/00–10; A62B 23/02–025; A62B 7/00–14
USPC .................................................... 128/206.12
See application file for complete search history.

(56) References Cited

U.S. PATENT DOCUMENTS

2021/0353790 A1* 11/2021 Abbaszadegan .......... A61L 2/04
2022/0001981 A1* 1/2022 DeFrank ................ B64U 10/13
2023/0256129 A1* 8/2023 Boland .................. G16H 50/20
239/102.2

FOREIGN PATENT DOCUMENTS

CN 108375530 A * 8/2018
WO WO-2021214682 A1 * 10/2021

OTHER PUBLICATIONS

Translation of CN 105771107. Accessed from PE2E-Search on Apr. 29, 2024. (Year: 2016).*

* cited by examiner

FIG. 3A Regular mask: High probability of Pathogens passing through to Nasal passage.

FIG. 3B ADAPT smart mask with compressed air: Moves the pathogens away from nasal passage.

FIG. 3C ADAPT smart mask with disinfectant/mist: Disinfectant/mist attaches to the pathogen and move them to the ground due to increased overall size.

FIG. 3D ADAPT smart mask with UVC: Ultraviolet – C rays destroy the pathogens in the air.

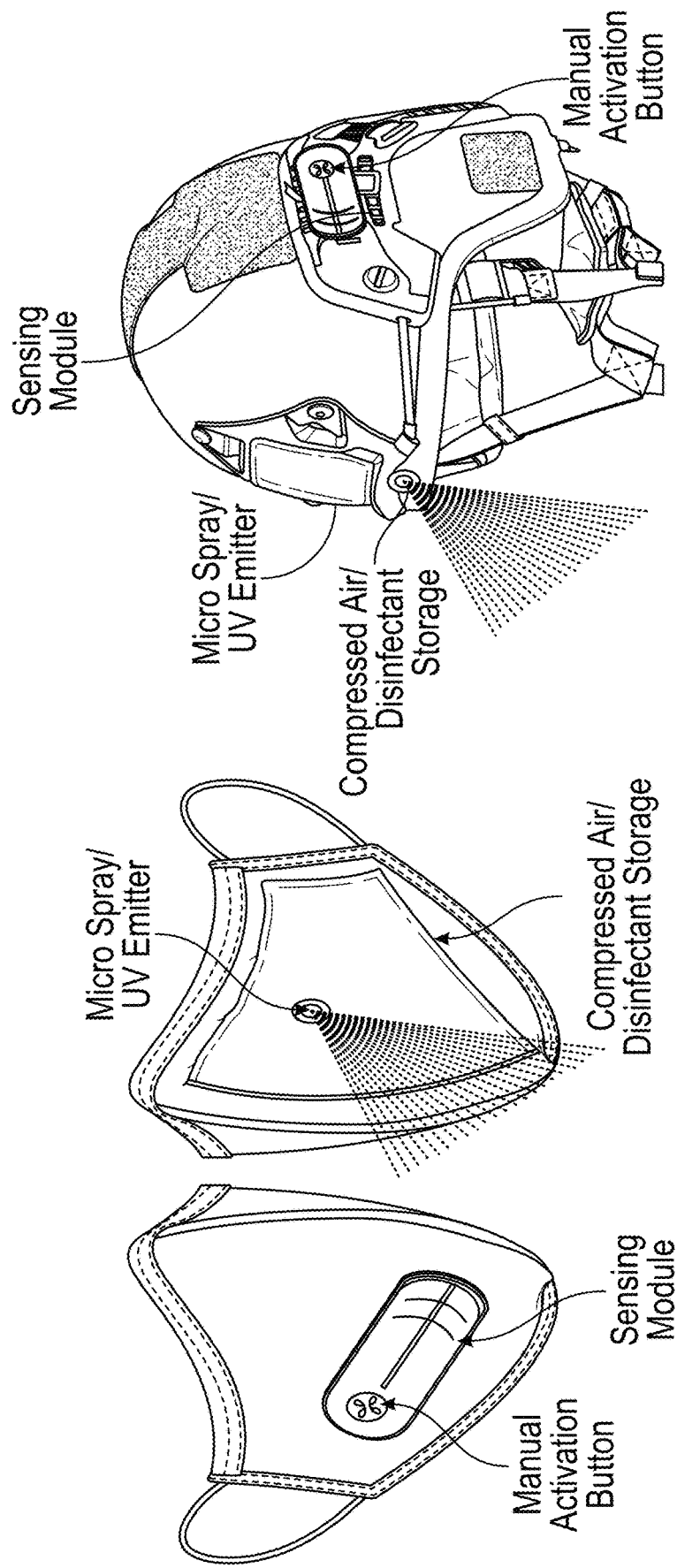

```
                Sensor                              Mitigator
         ┌─────────────────┐              ┌─────────────────────┐
         │  Aerosol detector │              │   Bluetooth          │
         │                   │              │   transmitter and    │
         │  Air quality       │              │   receiver           │
         │  analyser          │              │                      │
         │  Encryption        │              │   Decryption         │
         │  Bluetooth         │              │   Data analyzer      │
         │  transmitter and   │              │   Mitigation device  │
         │  receiver          │              │   (Disinfectant/UV   │
         │                    │              │    spray)            │
         └─────────────────┘              └─────────────────────┘
```

Control line
Data line

FIG. 6

```
Mitigation module
                    ┌──────────────┐
                    │   Receive    │      • V_cur = Amount of virus
                    │ Wireless data│        present
                    │   receiver   │      • V_th = Safe amount of virus
                    └──────┬───────┘      • Dis_req = Amount of
                           ↓                disinfectant required
                    ┌──────────────┐      • Dis_av = Amount of
                    │  Get aerosol │        disinfectant available
                    │   quantity   │
                    └──────┬───────┘
          Method           ↓
┌───────┐         ◇ Method ◇──UV──→ ┌─────────────┐
│Control├────────→                   │  Measure UV │
│       │         Spray↓             │   emission  │
└───┬───┘                            │   required  │
    │         ┌──────────────┐       └──────┬──────┘
Dis_av        │   Measure    │              ↓
    │         │ disinfectant │         ◇Sufficient◇──Yes─┐
    │         │   required   │         ◇ battery? ◇      │
    │         └──────┬───────┘              │No          │
    │                ↓                      ↓            ↓
    └────→ ◇Dis_req<Dis_av◇──No──→  ( Replace )    ( Emit UV )
                     │                ( Battery )
                   Yes↓                   
              ( Spray     )        ( Replace       )
              (disinfectant)       ( disinfectant  )
```

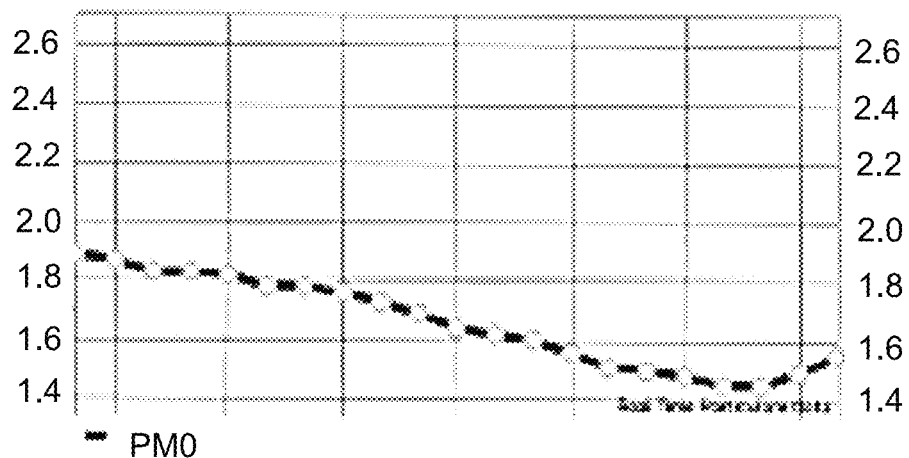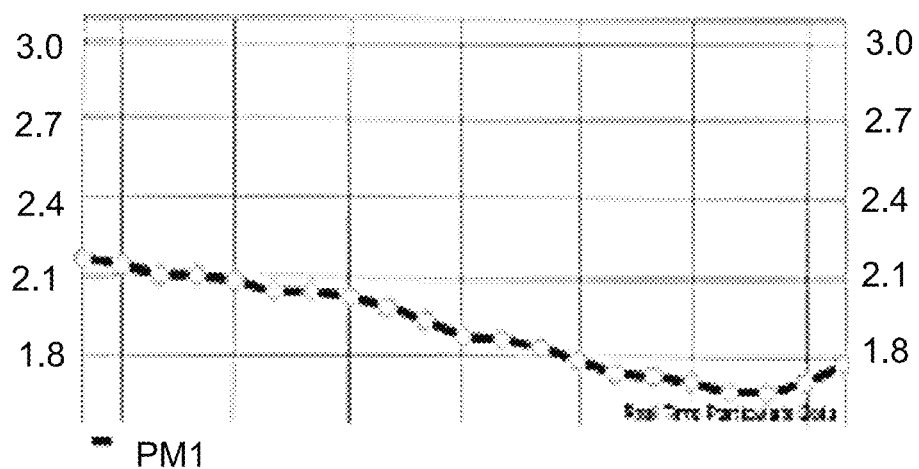
FIG. 18H

SYSTEM AND METHOD FOR CLOSED-LOOP ACTIVE SENSING AND PROTECTION AGAINST AIRBORNE PATHOGENS

CROSS-REFERENCE TO RELATED APPLICATIONS

This application claims the benefit of U.S. Provisional Application No. 63/049,798, filed Jul. 9, 2020 and titled "SYSTEM AND METHOD FOR CLOSED-LOOP ACTIVE SENSING AND PROTECTION AGAINST AIRBORNE PATHOGENS," the entire contents of which is hereby incorporated herein by reference.

BACKGROUND

A single infectious disease can ravage communities around the world in a short amount of time. For example, coronavirus disease 2019 (COVID-19) brought the lives of numerous individuals to a standstill and the economies of the most powerful nations to their knees. Without a vaccine available, most people actively followed social distancing norms, proper hygiene, and other preventive measures. However, these preventive measures are tough to maintain and may have severe and long-lasting social and economic consequences. It will be beneficial to find a way to combat the deadly virus and continue with our daily lives actively. Communities cannot rely on just preventive measures to defeat highly contagious diseases in scenarios in which there is a long delay until a vaccine becomes available.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIGS. 3A-3D illustrate various embodiments of the active mitigation of a mask article, according to one embodiment described herein.

FIG. 4A illustrates a mitigation system attached to a mask, according to one embodiment described herein.

FIG. 4B illustrates a mitigation system attached to a helmet, according to one embodiment described herein.

FIG. 6 illustrates block diagrams of a sensor device and a mitigation device, according to one embodiment described herein.

FIGS. 7A and 7B are flowcharts of a sensing application and a mitigation application, according to one embodiment described herein

FIG. 9 is a block diagram of a laser inducted fluorescence (LIF) system, according to one embodiment described herein.

FIG. 18H illustrates graphs for visualizing data received from the mask apparatus, according to one embodiment described herein.

DETAILED DESCRIPTION

Figure 1:
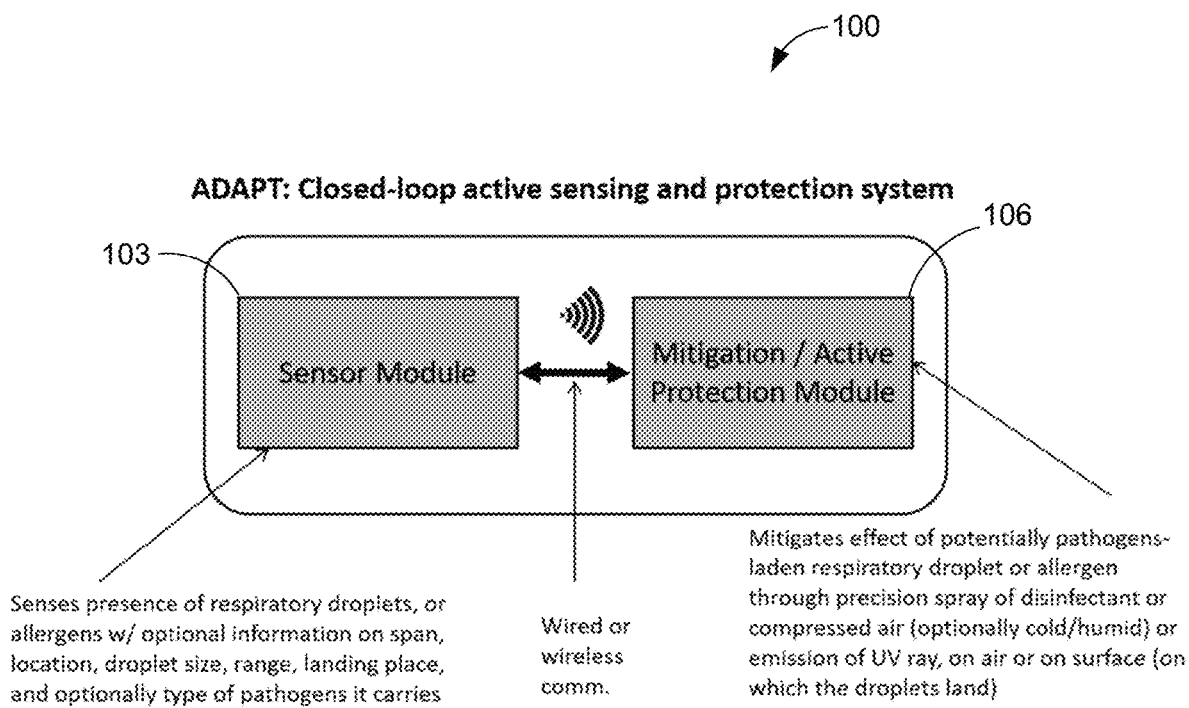
FIG. 1 is a block diagram of an active mitigation system, according to one embodiment described herein.

The present disclosure relates to various embodiments of systems and methods for an active defense against air-borne pathogens. For example, some embodiments implement an active anti-virus device by providing closed-loop active protection against airborne pathogens, including infectious diseases such as the novel coronavirus, influenza, measles, etc. FIG. 1 provides one non-limiting example of an overview of a mask apparatus, such as an active defense against air-borne path (ADAPT) system 100. The ADAPT system 100 comprises a sensor module 103 and a mitigation module 106. The ADAPT system 100 senses environmental parameters to detect the existence of potentially pathogen-laden aerosol droplets floating in the air (originating from infected people) and, based on the sensed parameters, takes immediate action to kill the pathogen.

In some embodiments, the mitigation module 106 can be positioned inside a mask, which can be injection molded or 3D printed. The mitigation module 106 can include a liquid reservoir for holding a disinfect solution and the piezoelectric transducer. The sensor module 103 can include the particulate matter (PM) sensor, the microcontroller, a battery, and other suitable components. For example, some other components in the sensor module 103 can include a relay, oscillator, and amplifier for driving the transducer. The PM sensor can use a small built-in fan for self-cleaning. The piezoelectric transducer can be disc-shaped and can include a fine vibrating mesh sandwiched between two electrodes (one facing the water reservoir and the other facing the environment). Fluid pressure in the reservoir can be kept low, allowing surface tension to prevent water leakage through the mesh. The mitigation module 106 can generate mist by vibrating the transducer around its resonant frequency (110 kHz) to generate a pressure drop across the mesh. The data acquired by the PM sensor is shared with the microcontroller using an I2C bus. This data is transferred to any computing device via Bluetooth. In our case, the data is transferred to an Android application. This application can help the wearer to manually control the mitigation module 106, whereas in some examples the application can be configured for auto-detection mode. The application can also enable the user to either use it as a regular mask by turning off the active protection (e.g. the mitigation module 106). The data collected by the application can be used to update the active defensive properties custom to the current environment. A special function in the application can monitor the mobile device's built-in microphone to detect relevant audio cues and switch ON the mitigation module if necessary (e.g., when a sneeze or cough is detected).

The mitigation module 106 can use a cold mist generated by the piezoelectric transducer, which loads the particles, increasing their aerodynamic diameter and mass. This action makes them quickly fall to the ground. The settling time (ts) of the aerosols scale as d-2 making the proposed mitigation method particularly effective for smaller particles (d<0.3 µm) that are not efficiently filtered by masks. For example, settling time is in both still and turbulent air decreases from 130 hours for d=0.3 µm to only 8.2 minutes for d=10 µm. However, particles of a given size have similar settling time in still air, while in turbulent air, the probability of settling increases exponentially with time. Additionally, the mist spray produces an airflow pattern that actively blows droplets away from the user.

The embodiments of the present disclosure can be implemented in various manners. Some non-limiting examples that will be described later include (a) a smart mask, where both the sensor module 103 and the active mitigation module 106 are integrated within the mask; and (b) a smart helmet where both the modules 103, 106 are placed on headgear (a helmet or cap); and (c) a stationary, portable smart device to automatically disinfect common areas. Alternative arrangements, e.g., a sensor module 103 in the mask and a mitigation module 106 in the helmet, are possible. Besides, the placement of a portable version of the proposed closed-loop system 100 in strategic places, such as on a vulnerable surface (e.g., a dining table) where virus-laden droplets may land, is possible and can be highly beneficial.

The closed-loop automatic sensing and precise mitigation system (i.e. ADAPT system 100) can be installed near places where respiratory droplets, potentially virus-laden, may fall, from infected people and subsequently touched by many. For example, bathroom, doctor's waiting office, daycare, public transport such as bus, etc. The system 100, when placed in strategic places, can detect such droplets, and mitigate through spraying disinfectant or emitting UV rays. The mitigation techniques employed by the ADAPT system 100 can match the location, spatial span, and the number of droplets. That is, the angle at which the disinfectant is sprayed using a micro nozzle, or UV rays emitted, the intensity, and the duration will be tailored to the sensed data. Such active protection can kill the viruses while they remain airborne and before they can infect others, thereby eliminating the need for "blind" disinfection of these areas periodically, while being safer to touch these surfaces.

Figure 2:
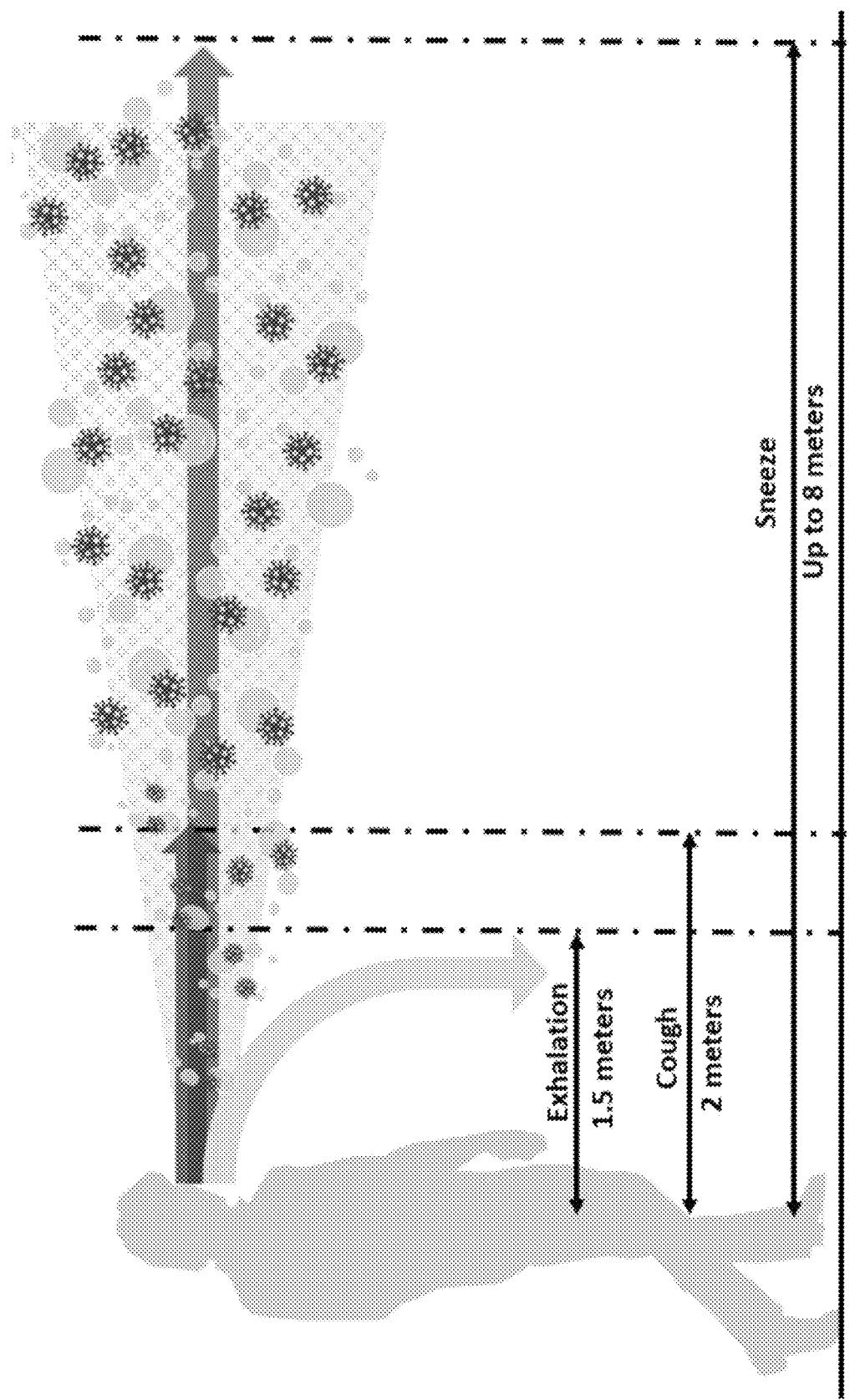
FIG. 2 is drawing that illustrates a spread of particles releasing a human body, according to one embodiment described herein.

Naturally produced droplets from humans (e.g., droplets produced by breathing, talking, sneezing, coughing) include various cell types (e.g., epithelial cells and cells of the immune system), physiological electrolytes contained in mucous and saliva (e.g., Na+, K+, Cl−), as well as, potentially, various infectious agents (e.g., bacteria, fungi, and viruses). Droplets >5 µm can be inhaled and these droplets tend to remain trapped in the upper respiratory tract (oropharynx nose and throat areas). In contrast, droplets ≤5 µm have the potential to be inhaled into the lower respiratory tract (the bronchi and alveoli in the lungs). According to some research, sneezing may produce as many as 40,000 droplets between 0.5 µm-12 µm in diameter that may be expelled at speeds up to 100 m/s and up to 8 meters, as illustrated in FIG. 2. Whereas, coughing may produce up to 3,000 droplet nuclei, about the same number as talking for five minutes. Infectious aerosols are generated when they come into contact and mix with exhaled air that may carry infectious agents from patients' respiratory tracts.

Droplet nuclei floating on-air may be carried by the movement of air. Entertainment of air into neighboring air spaces may occur during the most innocuous daily activities; for example, as a result of people walking, or the opening of a door between a room and the adjacent corridor or space. Also, the air temperature (and therefore air density) differences across an open doorway will cause air exchange to occur between the two areas. A higher temperature will create convective air currents that move from colder temperatures to warmer temperatures.

Based on all the information above, the phenomena of air current movement due to temperature differences can be used to decrease the number of pathogens inhaled through the active mask. A colder disinfectant spray can be used in the protection rather than the regular temperature for better protection. Also, masks can be used, which are colder on the outside, so that the air currents always flow away from the mask. Also, it is believed that when the disinfectant is sprayed, most of the pathogens get entangled with the disinfectant, which, even when inhaled, would not be as dangerous as an active virus.

Additionally, virus particles do not float freely in the air, but are always suspended in droplet nuclei that are significantly larger than the virus itself. The SARS-CoV-2 virus is 100 nm in diameter, and can remain suspended within droplets >0:2 mmin size. Droplets >5 µm fall to the ground quickly, while very small droplets evaporate and aerosolize in a few seconds to droplet nuclei ~1 µm in size. Fortunately, most masks can filter out droplets of this size: many materials have ≥96% filtration efficacy for particles >0:3 µm, including 600 TPI (threads per inch) cotton, cotton quilts, and cotton layered with chiffon, silk, or flannel. Thus, one important aspect for the proposed mask embodiments is to eliminate the small (but potentially significant) fraction of virus-laden droplets that are <0:3 µm in size. These small droplets are removed by creating an air-flow pattern close to the mask, through spraying a mist, that blows the droplets away from the wearer and also "loads" them (i.e., increases their mass and size), thus causing them to quickly fall to the ground.

Next, a discussion of the sensor module 103 (e.g. sensing device) for the ADAPT system 100 is provided. In some embodiments, the sensor module 103 can be represented as a particulate matter (PM) sensor. Methods for sensing airborne pathogens and allergens can be divided into sampling-based (local) approaches and remote detection approaches. A variety of pre-concentration and sampling methods based on solid impactors, liquid impactors, and filters are available. These methods have the advantage that the sampled pathogens can be analyzed, identified, and quantified using sensitive lab-based techniques such as real-time polymerase chain reaction (RT-PCR) or surface-enhanced Raman spectroscopy (SERS). However, incorporating such sensitive detectors into a wearable form factor is extremely difficult. Thus, a remote detection approach can be used for various embodiments.

Remote (also known as stand-off) detection of pathogens has been demonstrated using a variety of optical methods, using asymmetric microsphere resonant cavities, laser-induced fluorescence, and random Raman lasing, as well as non-optical methods such as THz imaging and spectroscopy. In some embodiments, a laser-induced fluorescence detector can be used. A laser-induced fluorescence detector can use light detection and ranging (LIDAR) to monitor both elastically- and inelastically-scattered laser light at various ultraviolet (UV) and visible wavelengths (350 nm to 700 nm). Field trials on a desktop version of such a device have shown excellent results in both detecting and discriminating between various bio-aerosols at distances up to 400 m. A miniaturized, low-cost, and low-power version has been developed for integration on a wearable device (e.g. the ADAPT system 100). In some embodiment, a particular matter (PM) sensor (e.g. a sensor module 103) that makes use of laser scattering to precisely count airborne particles in multiple size "bins." In addition, the control algorithm also can use data from auxiliary sensors (such as relative humidity and temperature) while determining the optimal parameters for the mitigation device (i.e., mist generator), since aerosol travel distances depend on such environmental factors.

The mitigation module 106 (e.g., the mitigation device) can generate aerosolized mist on-demand using a piezoelectric transducer. A variety of liquids, including pure water or mixtures of water with various impurities (to increase droplet mass) or disinfectants, can be used to generate the mist. The best disinfectant for a given pathogen can be found using guidelines provided by the U.S. Centers for Disease Control and Prevention (CDC) and Environmental Protection Agency. Common disinfectants include diluted bleach, soap, and >70% alcohol solution. In the context of the present disclosure, a wearable device may include a mask, a helmet, a facial covering, and other suitable articles of clothing that can be worn on the human head.

The peak output power of the pulsed laser source can be significantly reduced (to the 100 mW level) since the required detection distance is only 1-5 cm, thus allowing it to be implemented using a surface-mounted laser diode. Besides, a miniaturized commercial LIDAR sensor can be used as the detector. Finally, low-power air temperature and relative humidity sensors can be used for real-time calibration of the LIDAR detector; such auxiliary sensors are required since aerosol droplet size, composition, and density are known to depend strongly on this environmental factors.

Next, a discussion of the mitigation module 106 (e.g. mitigation device) components is provided. FIG. 3A illustrates a regular mask in use. Regular masks have a high probability of pathogens passing through to the nasal passage. The mitigation module 106 can implement various techniques for mitigating the detection of air borne pathogens. For instance, the present disclosure of the embodiments includes a discussion of the use of compressed air, and the use of chemical disinfectants and emitting ultraviolet light, as three non-limiting examples.

FIG. 3B illustrates the use of compressed air as a part of the mitigation module 106. FIG. 3C illustrates the use of a disinfectant mist as a part of the mitigation module 106. With regard to the use of disinfecting chemicals, the Centers for Disease Control and Prevention (CDC) suggests the use of various disinfectants to minimize the risk of interaction with harmful pathogens, such as viruses. Different kinds of solutions can be used as household disinfectants. Each type of virus has a best-suited disinfectant as suggested by the CDC, and these can be found on the United States Environmental Protection Agency (EPA) website. Some of the most common household disinfectants are diluted bleach, soap, and >70% alcohol solutions.

There are different ways in which the disinfectants work, as illustrated in FIG. 3C. They differ in their mode of action of their antimicrobial ingredients. Even small differences in the concentrations of active chemicals can impact the action of a disinfecting chemical. In general, disinfectants have three mechanisms of action, i.e., ways in which they affect or kill a pathogen: (i) cross-linking, coagulating, and clumping; (ii) structural and functional disruption; and (iii) oxidation.

Alcohols can work as a disinfectant by using the processes of cross-linking, coagulating, and clumping. Alcohols are generally considered to be non-specific antimicrobial because of their many toxic effects. Alcohols cause cell proteins to clump and lose their function. Specifically, the cell membranes lose their structure and collapse, thereby killing microbes. The alcohol can be diluted with water for the optimum effect, as proteins are not denatured as readily with straight alcohol.

Chlorine works as a disinfectant by the process of oxidation. It is a very common disinfectant used in a wide variety of cleaning solutions and applications, including drinking water because it exhibits fast bactericidal action even in minimal amounts. Chlorine works by oxidizing proteins, lipids, and carbohydrates. Chlorine compounds have also been shown to affect surface antigens in enveloped viruses and deoxyribonucleic acid (DNA) in non-enveloped viruses, thus causing structural alterations. Very few chemicals are considered sporicidal; however, chlorine compounds in higher concentrations have been shown to kill bacterial spores such as Clostridium difficile.

Peroxygen compounds use the process of oxidation to work as disinfectants. Both hydrogen peroxide and peracetic acid are peroxygen compounds of great importance in infection control because, unlike most disinfectants, they are unaffected by the addition of organic matter and salts. Besides, the formation of the hydroxyl radical, a highly reactive ion that occurs as peroxygen compounds encounter air, is lethal to many species of bacteria because it is a strong oxidant. Being highly reactive, the hydroxyl radical attacks essential cell components and cell membranes, causing them to collapse. Peroxygen compounds also kill spores by removing proteins from the spore coat, thus exposing its core to the lethal disinfectant.

Similar to alcohol, phenols' mechanism of action is cross-linking, coagulating, and clumping. Phenol and its derivatives exhibit several types of bactericidal action. At higher concentrations, the compounds can penetrate and disrupt the cell wall and make the cell proteins fall out of suspension. One of the first effects is the deactivation of essential enzymes. The next level of damage to bacteria is the loss in the membrane's ability to act as a barrier to physical or chemical attack.

Quaternary ammonium compounds (quats) are some of the most widely used disinfectants today because of their broad-spectrum effectiveness. Quaternary ammonium compounds work by denaturing the proteins of the bacterial or fungal cell, affecting the metabolic reactions of the cell and causing vital substances to leak out of the cell, causing death.

Moving on, a discussion of the use of ultraviolet (UV) light by the mitigation module is provided, as shown in FIG.

3D. The use of UV light for killing bacteria and viruses has been studied in detail. UV light, which is often used in conventional devices available on the market to clean household objects, is effective in laboratory studies at killing bacteria on computer screens, toothbrushes, food, and other objects. It has also been shown to affect viruses in similar ways, FIG. 3D. UV light, because of its relatively high frequency (i.e., short wavelength), is lethal for bacteria and viruses. In particular, UV light can damage the nuclear material of pathogens by generating mutations. Such mutations tend to degrade the reproductive capabilities of pathogens, thus eradicating them from the irradiated surface or volume. Germicidal UV or UV-C is part of the ultraviolet spectrum. It is best known for its ability to inactivate pathogens like bacteria and viruses. It can utilize specific wavelengths of the ultraviolet spectrum, typically between 200 nm-280 nm. Germicidal UV is typically used to disinfect rooms and surfaces. COVID-19 and other infectious diseases can live on particular surfaces for up to three days, so it is critical to disinfect at regular intervals.

Recently, the use of UV-C with a wavelength of 220 nm has gained momentum as a disinfectant for killing bacteria, pathogens, and viruses. One example of this technology has been developed by Columbia University's Centre of Radiological Research. It uses lamps to emit continuous, low doses of UV-C that kill viruses and bacteria without harming human skin, eyes, and other tissues (due to the short penetration depth of UV-C), thus eliminating the well-known problem of tissue damage associated with exposure to conventional UV light at longer wavelengths.

Next, a discussion of various embodiments of the ADAPT system 100 is provided. In one embodiments, among others, a smart mask, as shown in FIG. 4A, is a wearable device configured to protect the parts of the human body that are most vulnerable to airborne pathogens, namely the respiratory inlets (nose and mouth). Unlike traditional passive masks that merely impede the passage of minute (size=0.1 µm 10 µm) airborne droplets containing pathogens (viruses, bacteria, spores, etc.), a smart mask can be integrated with sensing and mitigation modules to mitigate such pathogens using compressed air, a disinfectant, UV-C light, and other suitable mitigation techniques. In the various embodiments, the sensing and mitigation modules can be attached to the inside of one side of the mask. In contrast, the other side can have a provision for storing disinfectant spray (if a spray module is integrated for providing additional protection). In some examples, the latter is omitted if the mitigation module relies solely on UV-based eradication. The size of liquid (e.g., water, disinfectant, etc.) droplets that mix with a compressed gas (e.g., compressed air) can be customized for different concentrations of spray based on the extent of the situation (e.g. the quantity of pathogen in the airborne aerosol droplet). Also, the liquid droplets can be programmable in terms of droplet size. This will allow for targeting specific pathogens as well as allergens. All the embodiments of the ADAPT system 100 can be equipped with a manual activation button (FIG. 4B). This feature can be used if the user feels the requirement of continuous protection without waiting for the sensor module to use the mitigation module. In this case, the mitigation module 106 might continue to spray for a specific period. Also, by taking advantage of the user's location by using Wi-Fi inside the hospital or house, the mitigation module 106 can automatically set to spray if the user enters some potentially vulnerable areas.

Next, a discussion of a smart helmet embodiment is provided. In one example, the embodiment includes components of the ADAPT system 100 attached to a helmet. Similarly, in case of discomfort due to the overall weight of a smart mask, the sensing and mitigation modules can be integrated into headgear (e.g., a helmet or cap) instead. The smart helmet shown in FIG. 4B can be used along with a regular mask. This embodiment can have a sensor module 106, which can detect aerosol presence in the air, and a mitigation module which calculates the amount of disinfectant or UV radiation dose required to kill the virus or germs. Just as in a smart mask, the disinfectant storage unit can be used in scenarios in which the disinfectant is used as a protection method.

Figure 5B:
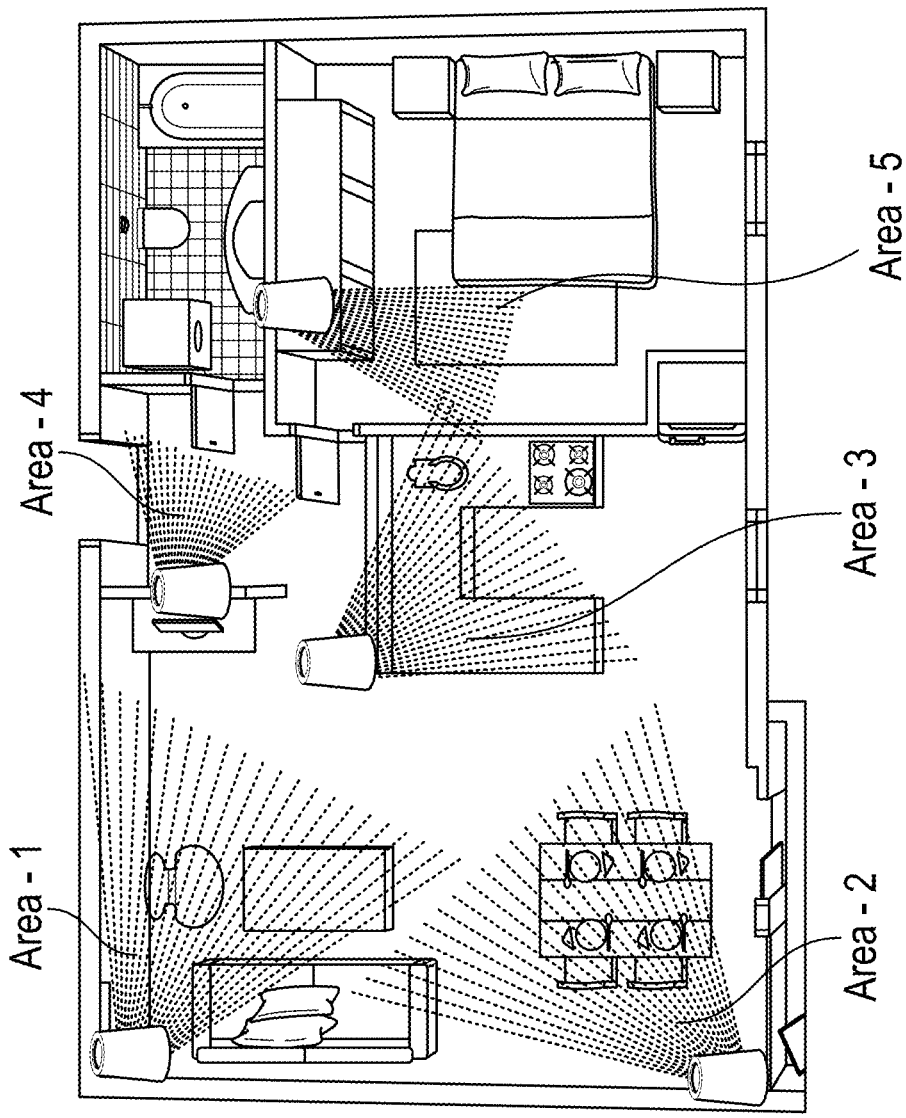
FIG. 5B illustrates multiple mitigation systems from FIG. 5A positioned in various locations, according to one embodiment described herein.
Figure 5A:
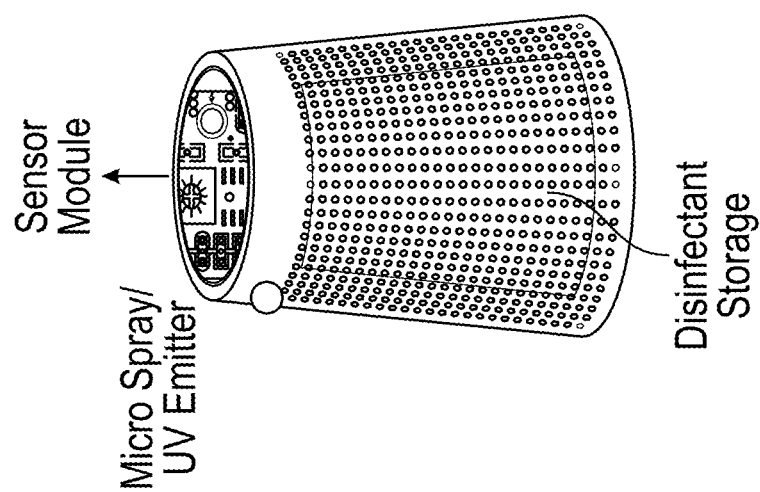
FIG. 5A illustrates a mitigation system as a stationary device, according to one embodiment described herein.

Next, a discussion of a stand-alone embodiment of the ADAPT system 100 is provided. In case of active protection at specific locations indoors, where there is a high chance of virus or germ accumulation, a smart stationary spray (FIG. 5A), which can sense the presence of harmful virus and germs, can be deployed. This device can measure the amount of disinfectant or UV radiation required to mitigate the virus. The system can then intelligently initialize the mitigation module in instances in which the sensor module 103 indicates the presence of harmful viruses, bacteria, or other pathogens. This active sensing and actuation approach can help in the judicious and targeted use of disinfectant, which eliminates the need to spray and wipe down all locations where there is a potential for virus accumulation (FIG. 5B); the resulting savings invaluable human resources (time and labor) are particularly significant for large buildings such as grocery stores and warehouses.

Moving on to FIG. 6, shown is a block diagram of the ADAPT system 100. A discussion of the system functionality of the block diagram is provided. In some the embodiments, a closed-loop active protection approach is used. For example, a system can include a sensor module 103 and a protection/mitigation module 106. There can be constant communication between the modules to detect and eradicate harmful pathogens (viruses or bacteria) in real-time. In another example, a system may include a controller that that controls the data communication between the sensor module 103 and the mitigation module.

The closed-loop system can integrate a sensor module 103, as shown in FIG. 6 that senses the presence of airborne aerosol droplets (typical diameter 0.1 µm 10 µm) in the immediate environment of the consumer's respiratory tract. It integrates an optical detector system (e.g., an aerosol detector) and auxiliary humidity and temperature sensors (as described previously) to quantify the sizes, pathogens, and concentration of these droplets as they approach the protected surface (i.e., the nose and mouth). The sensor module 103 can optionally integrate an additional airflow sensor further to quantify the rate of flow of respiratory droplets. The outputs of both sensors can be processed by an air quality analyzer module. The sensor module 103 and/or a controller can use a trained machine learning (ML) algorithm to analyze sensor data and thereby classify the quality of the incoming air stream based on health risk (e.g., "very high", "high", "moderate", and "low"). These risk categories can then be encrypted for security and sent to the mitigation module either wirelessly (e.g., over Bluetooth) or by using a wired connection.

Figure 7A:
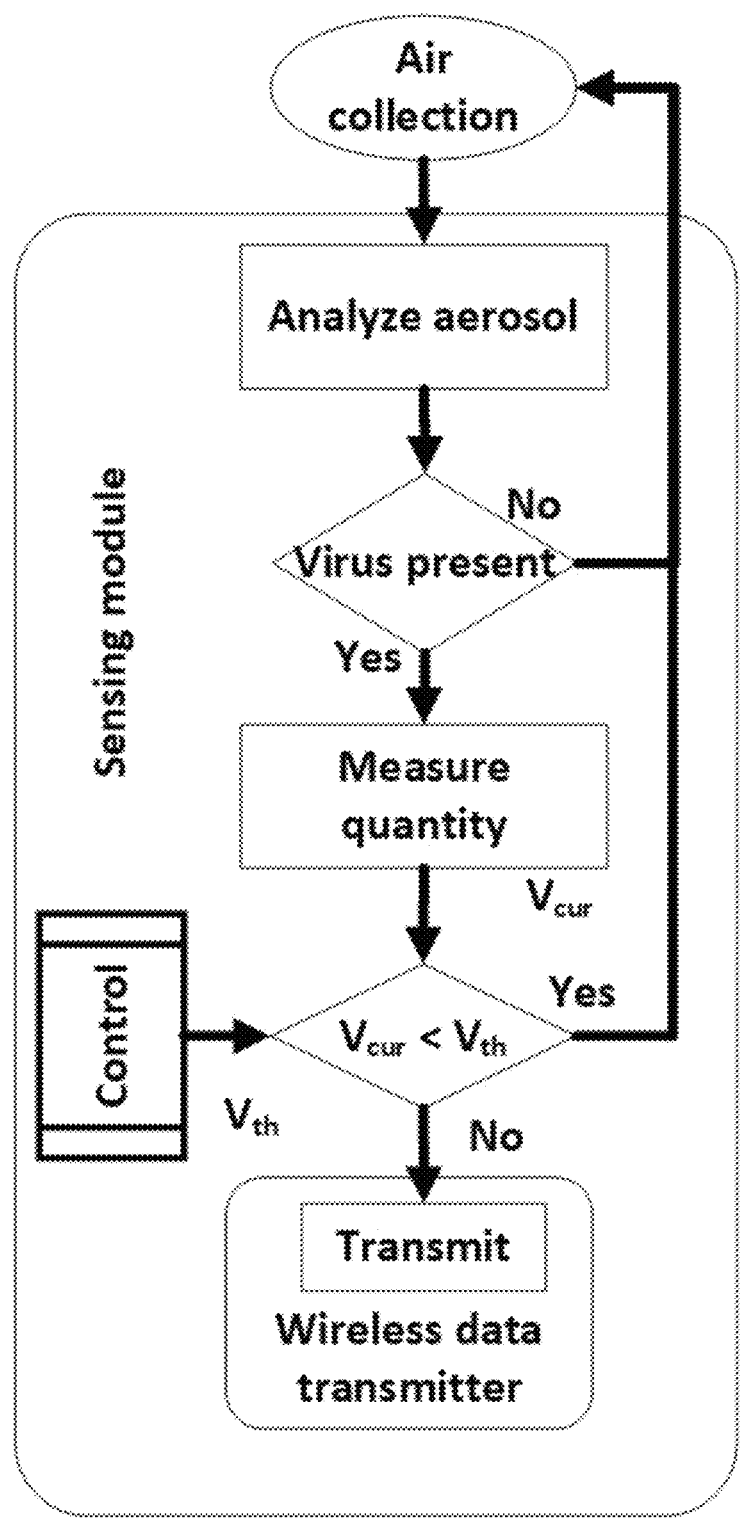
Figure 8:
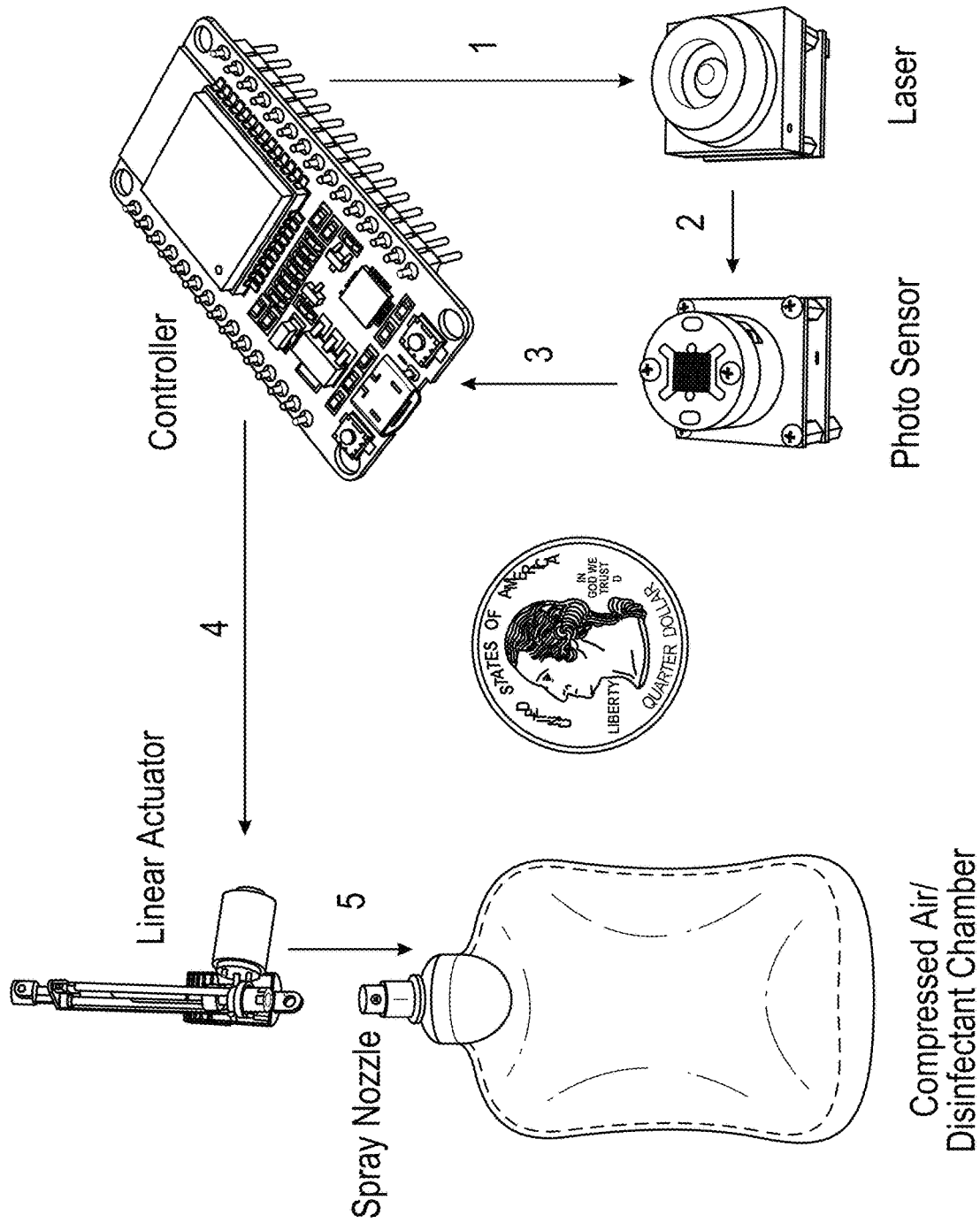
FIG. 8 is a block diagram of a prototype mitigation system, according to one embodiment described herein.

With reference to FIGS. 7A and 7B, shown are flowcharts for a sensing application and a mitigation application. The closed-loop system can integrate an active protection mechanism triggered by a "high risk" output from the sensing device, as summarized in FIG. 7A. The protection mechanism is based on combining two complementary approaches, as outlined earlier. A first approach can include spraying a disinfectant that is safe to human exposure by using a micro nozzle and a flexible chamber. For example, if the ADAPT system 100 is put on a mask, the chamber can be a flexible bag that can wrap around the mask surface. Alternatively, it can be integrated within headgear (the active hat concept), in which case it is triggered by an electromechanical relay driven by an electronic control unit that communicates with the sensing unit via a wired or wireless (e.g., Bluetooth) connection. Further, a second approach may include directing pulses of UV-C light generated using an array of UV light-emitting diodes (LEDs). Such UV LEDs have been shown to be a miniaturized and low-power alternative to disinfection using conventional mercury vapor lamps.

The hardware and software required for both sensing and mitigation modules can be implemented using low-cost off-the-shelf components (e.g. prototypes described later are comprised of a low-power microcontroller and a wireless system-on-module), thus enabling wide adoption and deployment by vulnerable individuals. Some embodiments of the hardware and software can also be integrated into other daily-use products, thus minimizing the potential discomfort caused by chronic use of a relatively heavy face mask. Further, some embodiments can be equipped with an additional ML algorithm that can learn when such respiratory droplets are likely to be present in a location and proactively employ the proposed active protection mechanism. This type of device can be useful for educated and targeted elimination of harmful pathogens from the near-human environment. The sensor inputs and the controller of the ADAPT system 100 can be connected to a cell phone through the wireless module. A wearer can monitor the status of the amount of remaining liquid from the cell phone, as well as allow the wearer to override the mitigation step, such as the ejection of the cold mist or compressed gas or disinfectant. The ADAPT system 100 can send an alert on a user's cell phone when it needs to be refilled.

Some embodiments can also be equipped with additional chemical sensors (e.g., electrochemical detectors) to determine the level or an amount of active protective agents present in aerosol droplets and use this information to i) warn users, and ii) control the release of disinfectant from the smart mask. The goal is to mitigate the potential negative impact on health due to exposure to or inhalation of elevated levels of disinfectants (e.g., those present in Lysol/Clorox/Bleach, etc.). Since there is a high level of use of such disinfectants by everyone, there is also a significant possibility of elevated levels of these chemicals being present in airborne aerosols, thus resulting in long-term health impacts. The embodiments of the present disclosure can mitigate such problems.

The embodiments of the present disclosure have various improvements over the existing implementations. For example, usually, passive masks act as a boundary between external pathogens, which can be easily bypassed. The embodiments can provide isolation and also kill the pathogens. In addition, the embodiments can be implemented as an active filtration system, while most masks have passive filters. The embodiments also can be implemented with a closed-loop system allowing it to respond to environmental cues rapidly and adapt itself to these environmental cues.

Additionally, the embodiments of the present disclosure have been designed with patchability in mind. As such, a component of or the entire embodiment can be upgraded, replaced or tweaked and reused at a component level. As a result, a non-smart filtration device can be retrofitted with aspects of the embodiments of the present disclosure. Further, the patchability of the embodiments allows for versatility. For example, the embodiments can be used to protect against airborne pathogens and also from various airborne allergens such as pollen and other harmful airborne particles.

Additionally, the embodiments can be made to fit any form factor such as face masks or even helmets, making it a plug and play solution for many applications. The embodiments can be made to fit in other apparel items and other wearable forms of protective equipment. Additionally, the embodiments can be equipped with multiple defense mechanisms making it more resourceful and convenient for many applications. For example, the defense can be organized in a tier manner. As such, the embodiments can assess the severity of a threat associated with airborne aerosol droplets and respond with a defense that is appropriate for the determined threat level.

Next, a discussion of a sensor element, such as a laser induce fluorescence technique, is provided. Laser Induced Fluorescence (LIF) is a technique to obtain a light measurement, e.g. a spectrograph, which can be used to collect spectrograph samples of the aerosols. The wavelengths scattered can then be used to identify the strain of the virus. The same method can be used to detect bacteria and some chemicals. Based on the wavelength analysis, the controller will decide to act or not.

Figure 9:
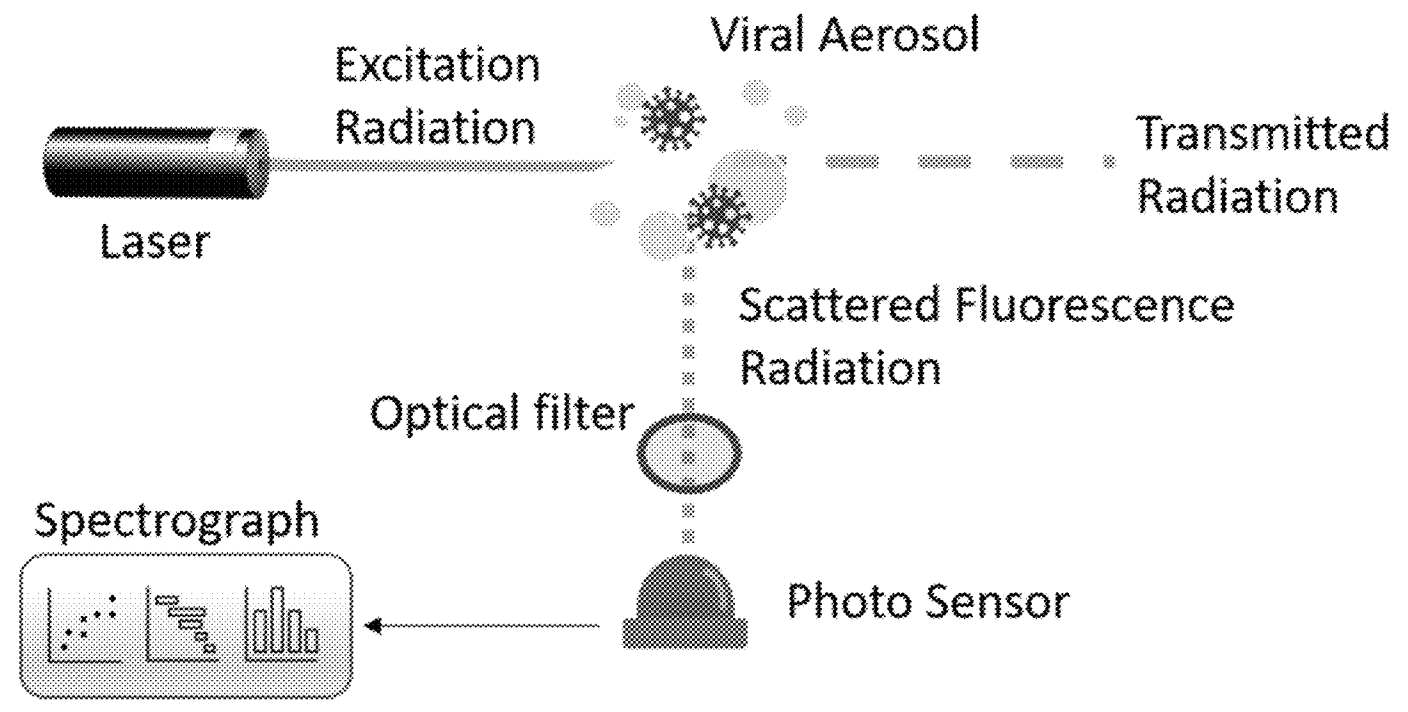

A LIF system (FIG. 9) consists of a laser that emits radiation that will excite the nearby air. If there is a presence of virological aerosol, the obtained or measured spectrograph can be used to identify it. Once the threat has been identified, a mask or element embodiment can either spray disinfectant, compressed air, or can also enable UV-C for killing the virus or bacteria present. Some of the potential sensing and mitigation modules can be seen in Table I.

TABLE 1

| Sensing | Mitigation |
| --- | --- |
| Laser | Compressed Air |
| Temperature | Cold Mist |
| Humidity | Disinfectant |
| Photoresistor | UVC |
| Raman Spectroscopy (benchtop) | |
| Lidar | |
| Asymmetric Microsphere Resonant Cavities | |
| Random Raman Lasing | |

Figure 10:
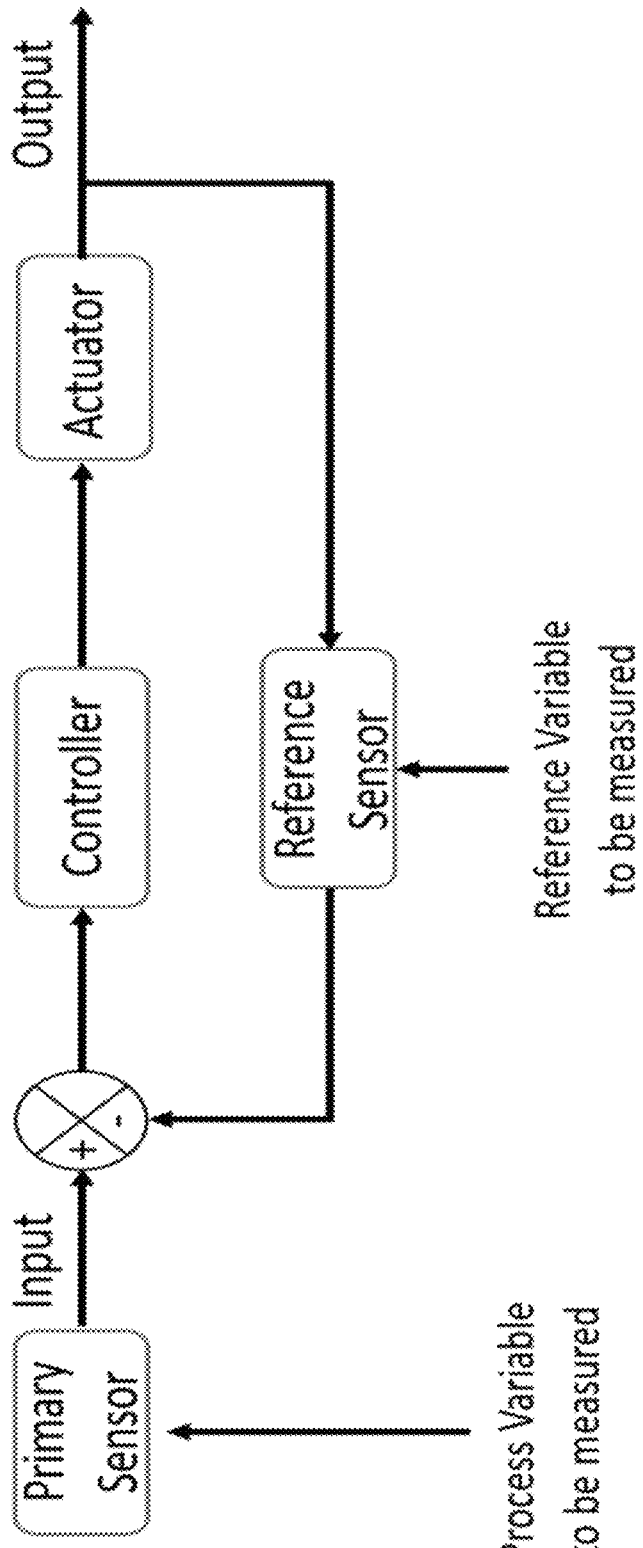
FIG. 10 is a block diagram of a closed loop control system, according to one embodiment described herein.
Figure 11A:
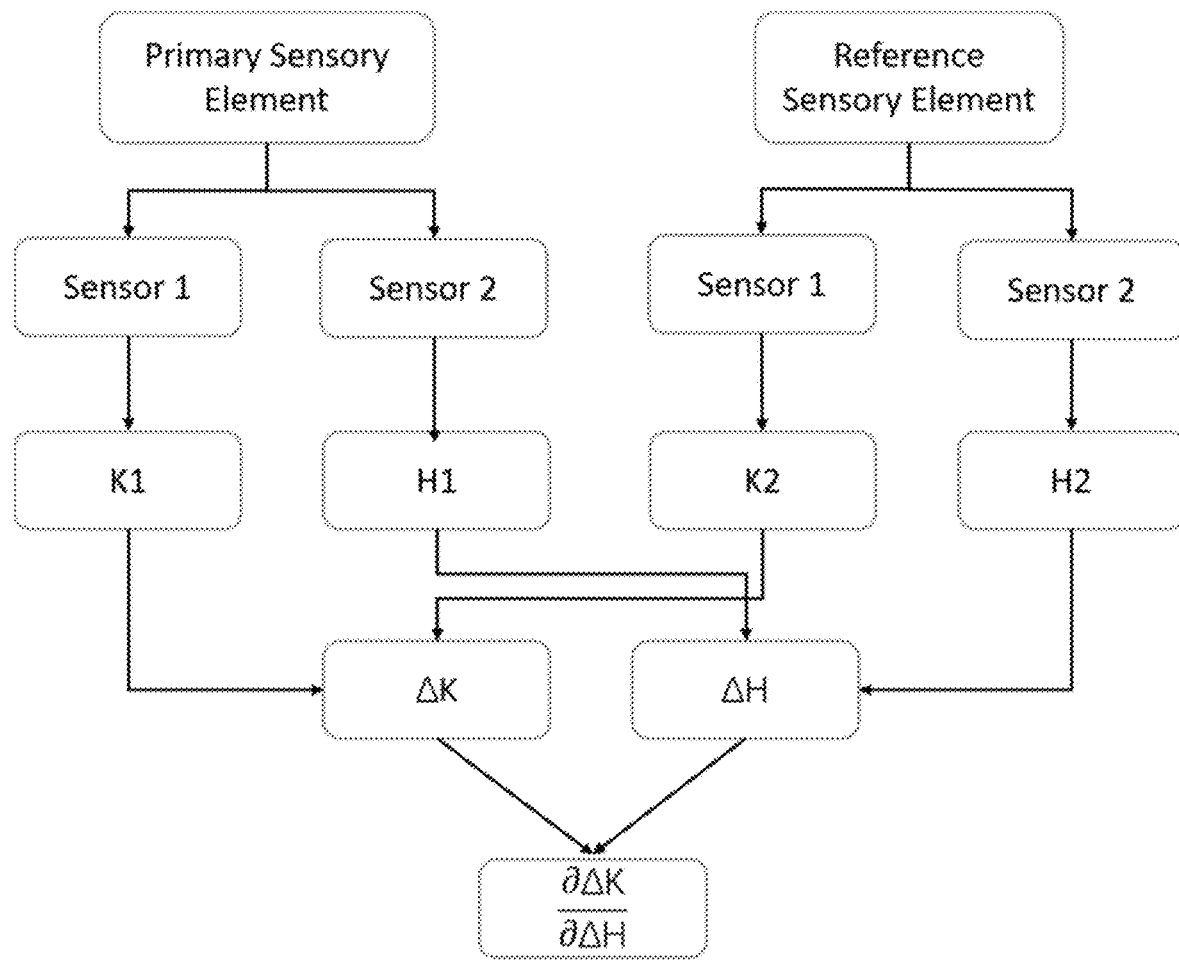
FIGS. 11A and 11B illustrates flow charts for the feedback control system, according to one embodiment described herein.
Figure 11B:
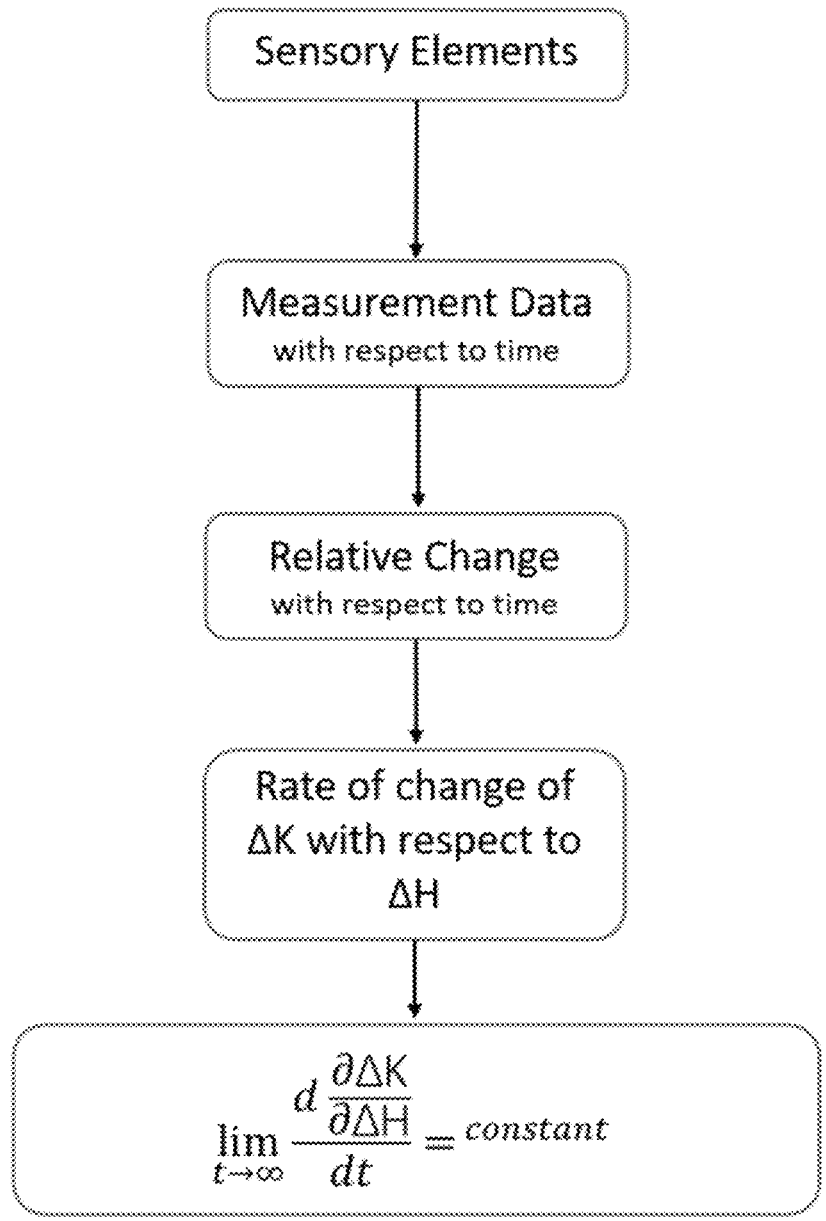
Figure 12:
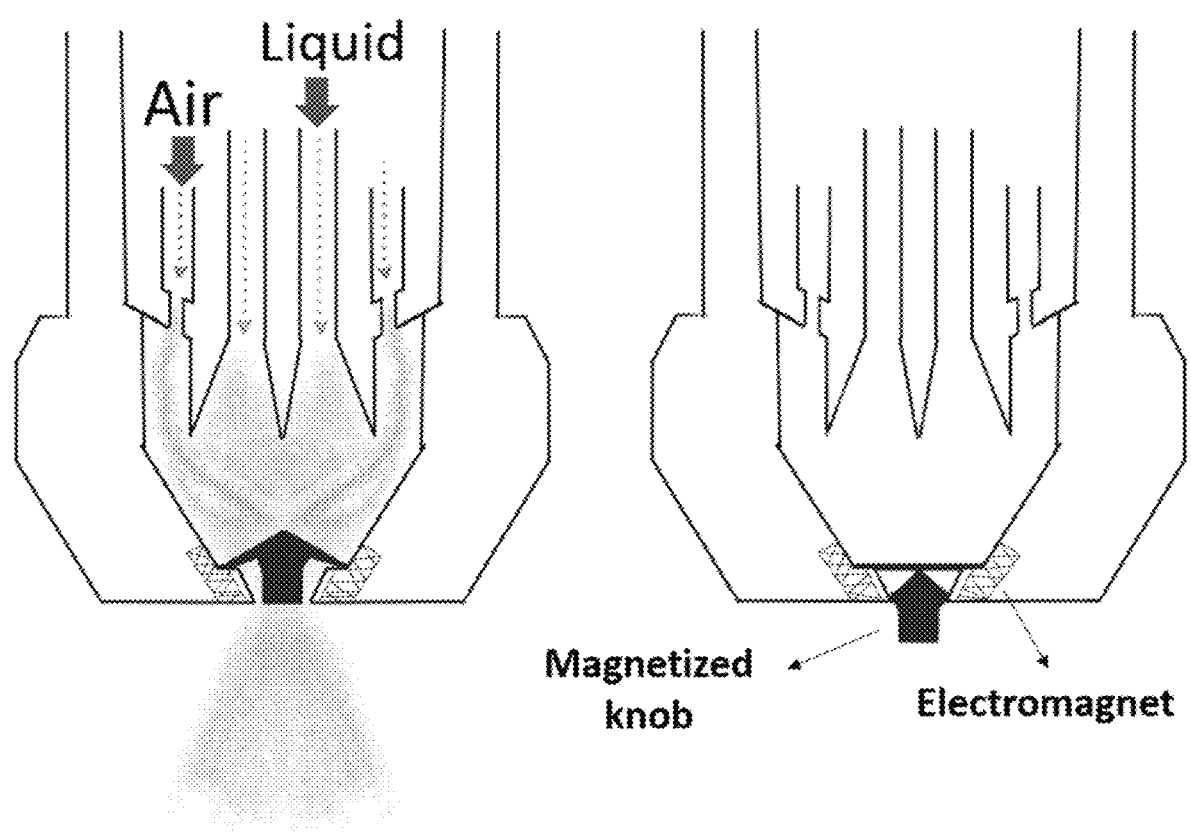
FIG. 12 illustrates cross sectional view of a spray nozzle. according to one embodiment described herein.
Figure 13:
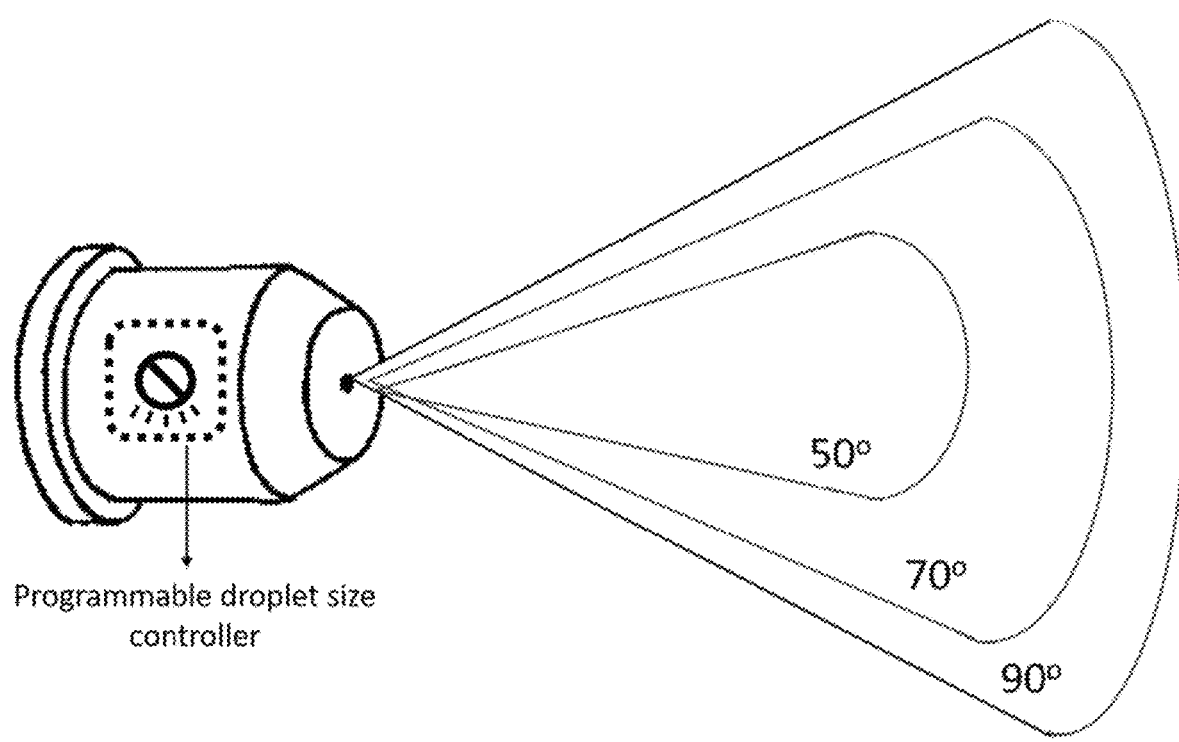
FIG. 13 is a drawing of a spray nozzle being adjustable, according to one embodiment described herein.
Figure 14:
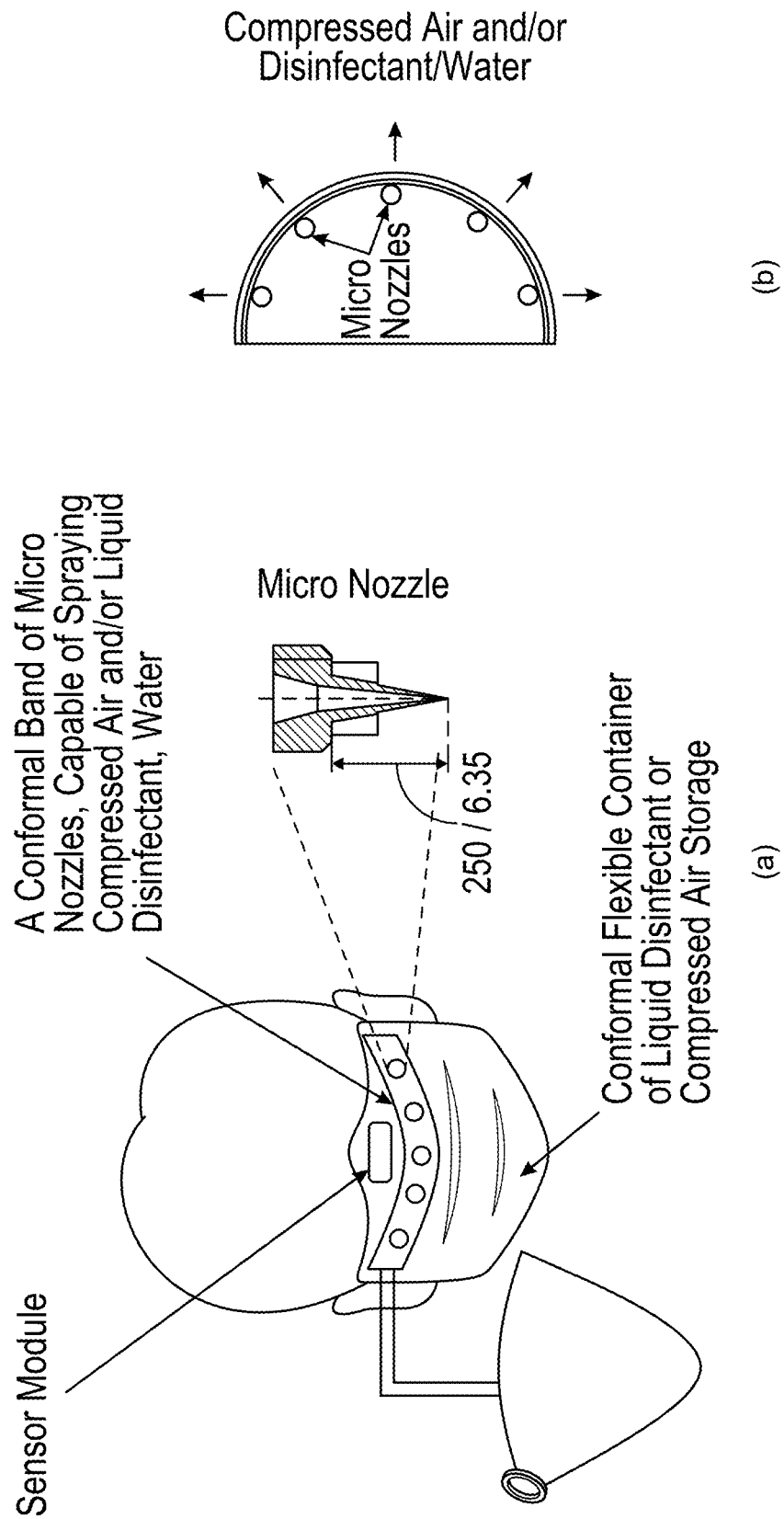
FIG. 14 illustrates exemplary embodiments of a mitigation mask, according to one embodiment described herein.
Figure 15:
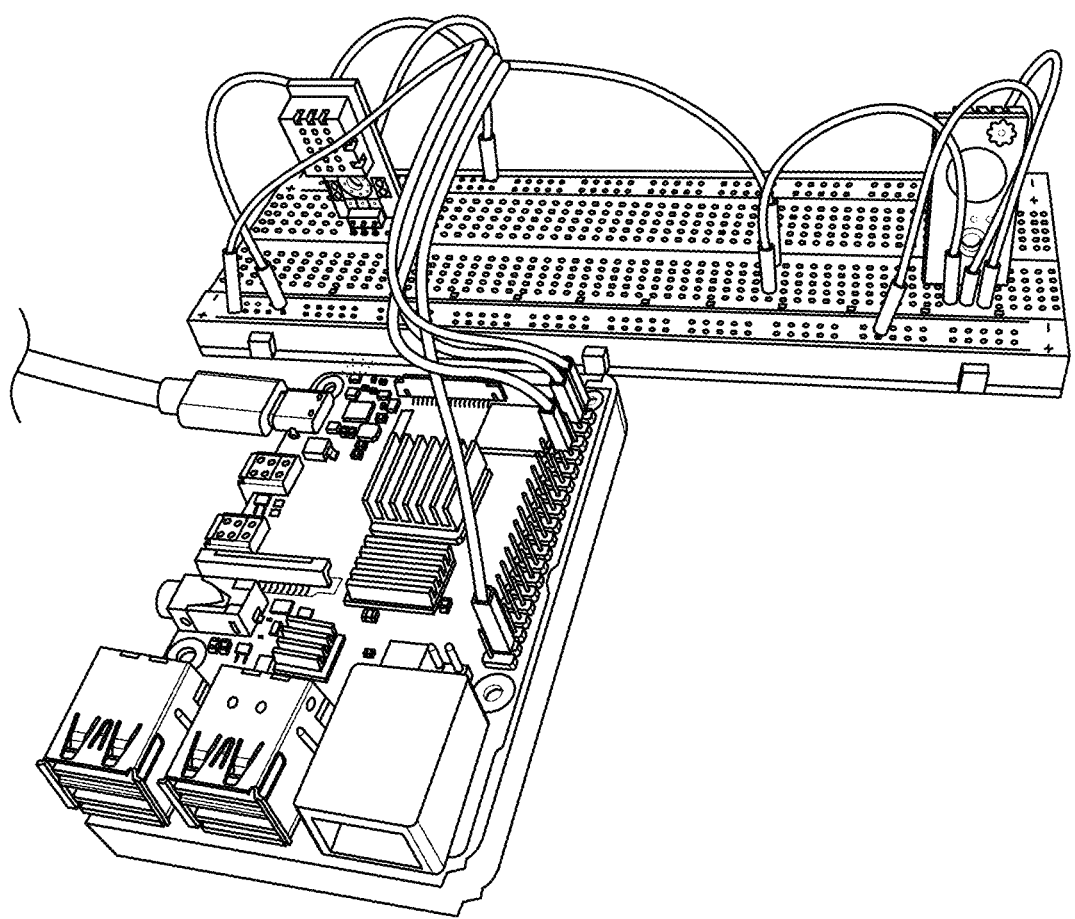
FIG. 15 depicts a prototype of a sensing device from FIG. 1, according to one embodiment described herein.

In various embodiments, the system can include a closed-loop functionality (FIG. 10), which assures for a continuous monitoring setup with feedback to control the amount of disinfectant to spray, compressed air to release, or other suitable mitigation technique. As such, the embodiments may be susceptible to process variations that are being measured and can still be efficient at employing mitigation methods.

In some example embodiments, a closed-loop system can be employed to identify the absence of the threat once a mitigation technique has been deployed. In many cases, a simple comparison between the inputs from two sensors will not be enough for effective operation. Oftentimes, the sensors cannot be physically identical due to manufacturing variations, and this can cause error irrespective of the output, which would send the system into a continuous loop. If f(x) is considered as the error function and e is the error, then the corresponding equation would be as follows:

$$f(x) = e(\Delta K, \Delta H) \quad (1)$$

In Eq.1, ΔK and ΔH represent the relative change of two process variables measured from the sensors. The dampening factor for Eq.1 is very high as there are inherent differences between the sensors, and they might persist after calibration. To overcome this, other variables affecting the sensor's output may need to be eliminated. In some embodiments, an algorithm can be employed to overcome this problem and can also be used to eliminate the constant calibration of the sensors.

Next, a discussion of the feedback control algorithm is provided. In the algorithm described below, the rate of change of the relative values of the variables can be obtained in order to eliminate longer dampening oscillations.

$$f(x) = e\left(\frac{\partial \Delta K}{\partial \Delta H}\right) \quad (2)$$

By using Eq.2, for calculating error, the dampening oscillations can be reduced for rapid control over the change of process variables. Now, the controller can monitor the outputs based on the trigger equation Eq.3. If the output satisfies Eq.3, then the controller exits the feedback loop.

$$f(x) = \lim_{t \to \infty} \frac{d\frac{\partial \Delta K}{\partial \Delta H}}{dt} = \text{constant} \quad (3)$$

Further, the ADAPT system 100 can also include spray nozzle actuation in some embodiments for mitigating the detected presence of air borne pathogens or for precisely controlling the air flow pattern around the ADAPT system, such that the airborne pathogens or allergens (e.g., pollens) move away from (and hence, do not contact) a PPE (on which the ADAPT assembly is mounted) or the face of the subject. In various embodiments, a new actuation mechanism for the spray nozzle can be employed to release compressed air or a disinfectant aerosol or water mist or any combination of them. The traditional spring valve nozzle sprays are bulky and require large actuation force. Some embodiments can use a magnetized knob attached to a valve to control the actuation mechanism. When the adjacent walls of the magnetized knob are magnetized using an electromagnet, as depicted in FIG. 12, the magnetized knob can rise into the cavity, which opens the valve. The opening of the valve can create a pressure difference, which can cause the compressed air to be released. If the disinfectant liquid is used, the liquid can mix with the air, and an atomized aerosol mixture is formed as it exits from the nozzle. The electromagnets on the walls of the nozzle can be actuated by the controller. Upon the detection of a hazard, the walls can be magnetized, and the aerosol or compressed air can be sprayed. In these embodiments, a linear actuator can be used in scenarios where size is not a constraint. Another advantage is that linear actuators can apply more force when compared to an electromagnetic actuator. The spray nozzle can have multiple applications. As is known, air currents can flow from lower to higher temperatures. The embodiment can spray cold or normal temperature water mists in front of the nozzle region for a specific duration of time to control the air flow and/or change the relative temperature in the user's pathway. These embodiments can be especially useful for caregivers who regularly encounter sick people. These embodiments can be realized using other systems like laser and ultrasound based actuation. Although the detection of pathogens in the air can be difficult using the ultrasound, this field of research is up-and-coming. The cold mist spray can also be installed at sensitive locations in the hospitals or public places. In public places, these embodiments can be mixed with disinfectant to consistently disinfect the place if the ultrasound machine detects if a person was in the vicinity. In hospitals, it can be used to disinfect places regularly visited places like patient rooms, waiting halls, reception area, and other suitable locations.

The nozzle can also be adjusted to spray at different angles. The aperture of the nozzle can be controlled, which would effectively change the spray angle (FIG. 13). By changing the spray angle, the embodiments can help control the range of the spray and to optimize the directionality of the spray. Wider angles of spray would travel lesser distances when compared to a narrow spray angle. But the wider spray angle covers a larger immediate space, whereas a narrow-angle is more focused. With the application of compressed air or disinfectants, the nozzle and the spray angle can also determine the velocity at which the fluids are sprayed. The nozzle also can be a programmable and customizable droplet size controller. This combination of versatility with control over droplet size and its spray angle provides precision control over how the fluid is sprayed, and the decision on these variables is taken by the controller based environmental factors. And as described in (FIG. 14), it represents an embodiment where a conformal band of micro nozzles are present on the mask, capable of spraying compressed air and/or liquid disinfectant, water.

In some embodiments, the ADAPT system 100 can use compressed air storage. A flexible rubber bag with reinforced walls can be used as a storage compartment. It can be either stored with compressed air or with a mixture of disinfectant in addition to it. Hydrofluoroalkanes can be used as the compressed air propellant, as one non-limiting example. The compound can comprise hydrogen, carbon, and fluorine atoms. With fair usage in inhalers, this propellant is safe to use at a medical standpoint.

Next, a discussion of an exemplary system setup and prototype are provided. The initial prototype of the system can be realized using the following components: Raspberry Pi 4, humidity+ temperature sensor, manual spray, and an infrared (IR) thermal camera system. To have a clear understanding of the physical system, it can be divided into three parts: controller, sensory element, and aerosol spray, as depicted in FIG. 8. The controller acts as the master for the other two components, giving them instructions on when to turn on the aerosol spray by processing the data collected from the sensory element. The aerosol spray mechanism has three sub-components for this exemplary embodiment. One such component is the storage chamber, which holds the aerosol mixture, a combination of compressed air, disinfectant, or both. The other two components are the spray nozzle and the actuator responsible for operating the nozzle. As shown in FIG. 12, the spray nozzle has four paths inside it with the outer two paths for air passage and inner two paths for the liquid disinfectant. The air and disinfectant liquid can mix under high pressure exiting from the nozzle as an aerosol. The sensory element in the prototype has a humidity and temperature sensor with a similar setup, as shown in FIG. 15. This example can be configured to measure two process variables so that the error function Eq.3 remains valid. The sensory element has five significant components categorized as Transmitter, Receiver, Digital to Analog converter(DAC), Analog to Digital converter(ADC), and a Digital Signal Processor(DSP). The humidity sensor has a built-in ADC to output digital values and also a DSP to output data directly to the Raspberry pi 4.

In this non-limiting embodiment, the measured temperature range is 0-50° C., and its accuracy is +/−2° C. The humidity measurement range is 20-90% RH with an accuracy of +/−5% RH. The experiment was carried out and collected 180 data points, where ΔH in the graph shows the relative temperature reading, and ΔK shows the relative humidity reading. The relative values are the difference between each value from the two individual sensors where one of the sensors is for the primary measurement, while the second one is for reference for the feedback loop.

FIGS. 16A and 16B shows the trends in the ΔH and Δk values respectively along with the error Eq.2 in FIG. 16C. The error function solely based on either ΔH or ΔK would have been useless considering the error from sensors not having the same initial conditions. FIG. 16C shows the trend of the error function Eq.3, where one can notice the oscillations, and it can also be see the dampening of the oscillations due to the actuation from the feedback loop.

Figure 17:
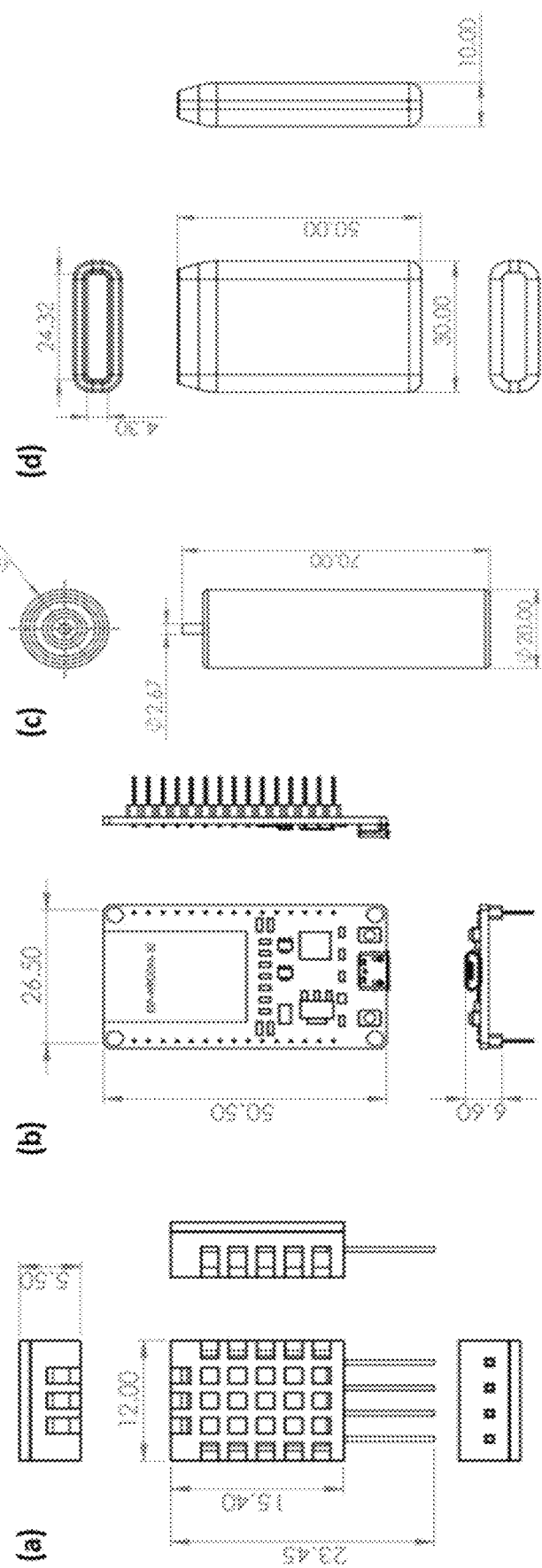
FIG. 17 illustrates component parts of a prototype of a mitigation system, according to one embodiment described herein.

FIG. 17 illustrates sizes of the various components. In some scenarios, the humidity and temperature can be continuously monitored in a specific region. The value of the humidity sensor can be directly related to the concentration of pathogens in the air. In the current scenario, as it pertains to the embodiments of the present disclosure, most pathogens can be transmitted using sneezes and coughs. During these situations, the pathogens are transmitted along with the cough droplets. These droplets can be detected using the humidity sensor. Also, the coughs and sneezes coming from inside the body may have higher temperature values, as seen from the ΔH value. Similarly, the LIF setup can be used where the temperature would directly affect the energy state of the aerosol being detected, and therefore produce different spectrographs than at average temperatures. So, the Eq.3 would remain valid during the operating of one of the embodiments of the present disclosure.

Figure 16:
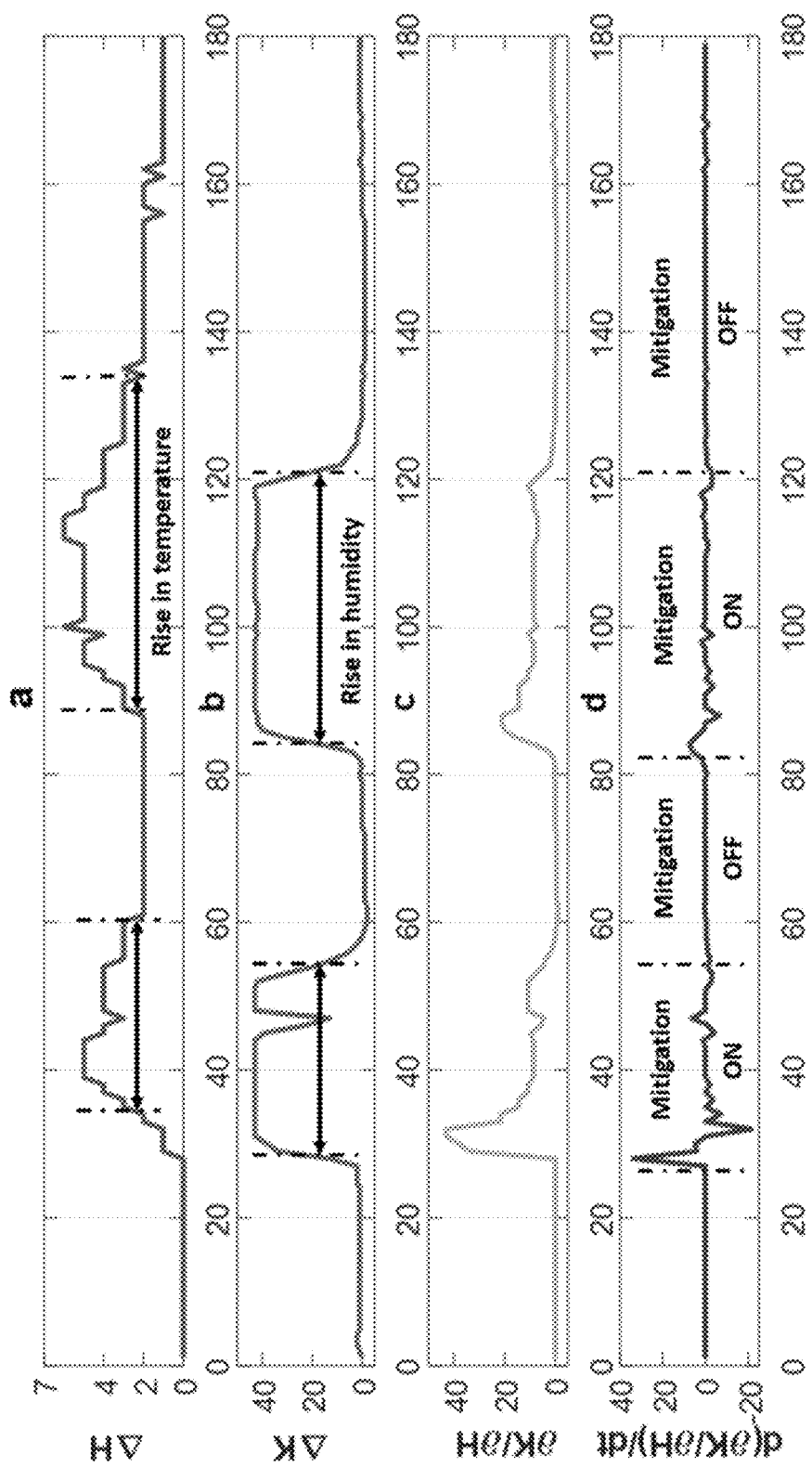
FIG. 16 are graphs of temperature and humidity over a period of time, according to one embodiment described herein.

When the controller detects the rise in ΔH and ΔK, the microcontroller can pass an instruction to initiate the mitigation process. At this point, the spray can be turned ON or activated. As this can be a closed-loop model, the spray can continue to be ON till it gets a signal from the microcontroller. Turning off the spray nozzle has been illustrated in FIG. 16D as the value of ∂ΔK tends to 0. As illustrated in FIG. 16C, when the error function in Eq.3 tends to become constant, the controller can instruct the aerosol spray actuator. Depending on the input from the feedback loop such as in Eq.2, the controller can control the amount of air/disinfectant to be discharged to kill the pathogens in its range. This has been proven in the prototype, and data plotted in FIG. 16 proves the results. The mask can be fit with this exemplary embodiment, which includes the controller, sensory elements, a flexible bag for storage of disinfectant/compressed air, actuators, and other suitable components.

Figure 18A:
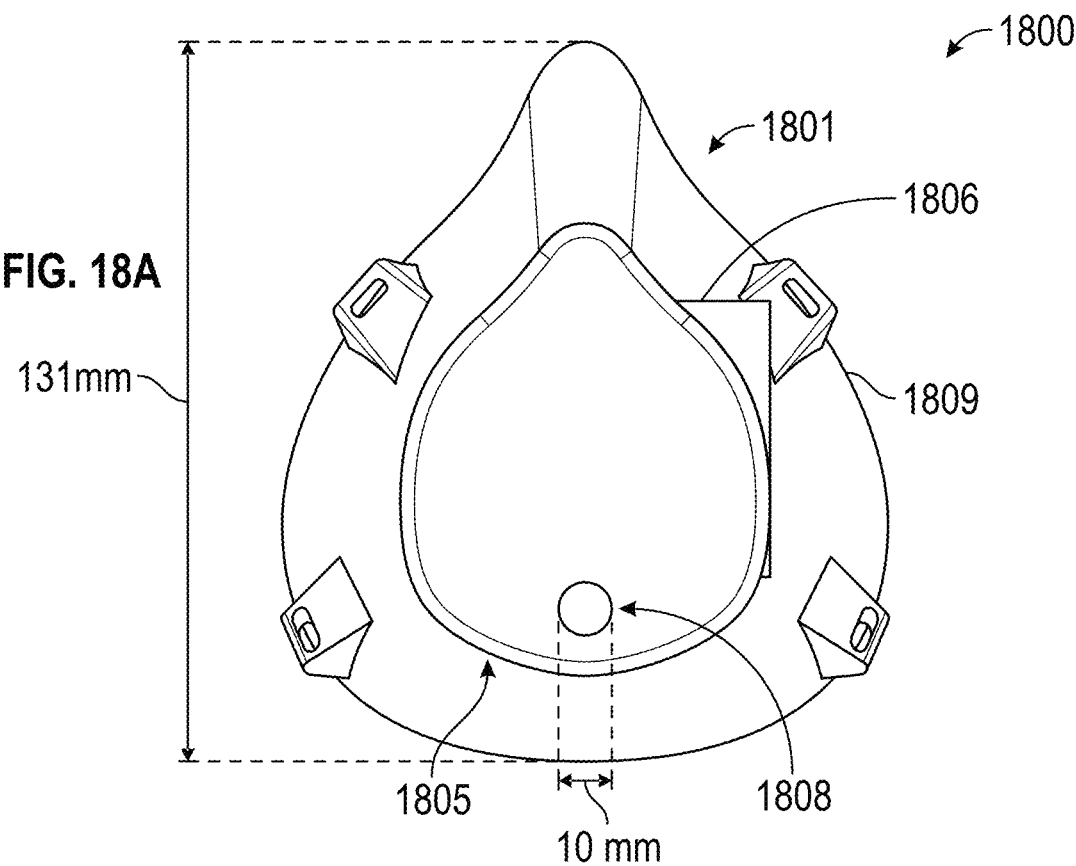
FIGS. 18A-18G illustrates various components of a mask apparatus, according to one embodiment described herein.
Figure 18B:
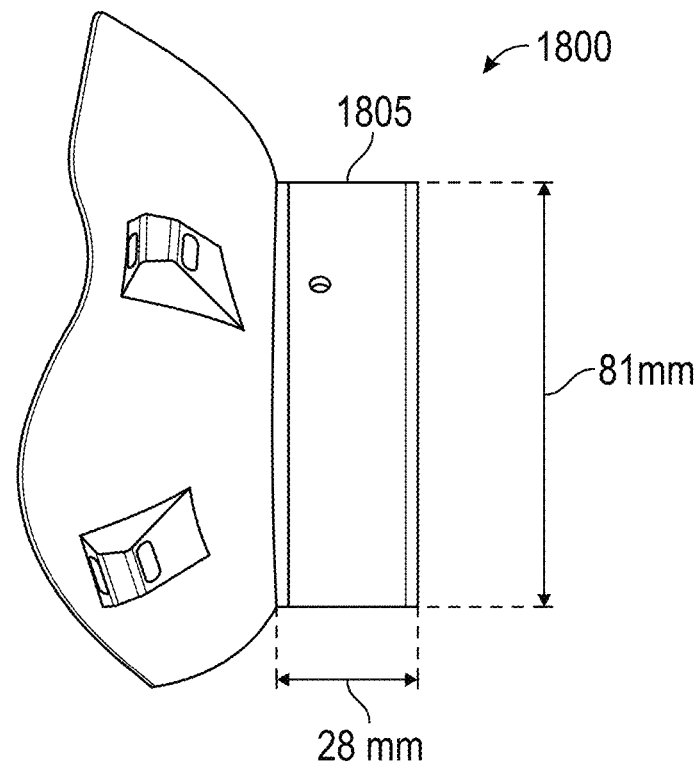
Figure 18C:
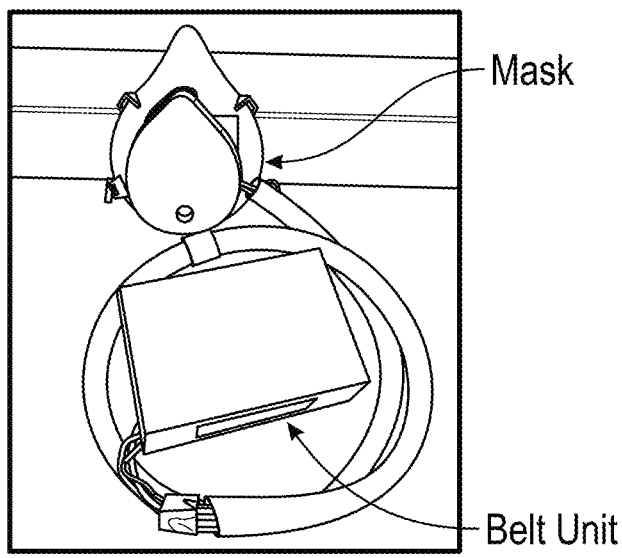
Figure 18D:
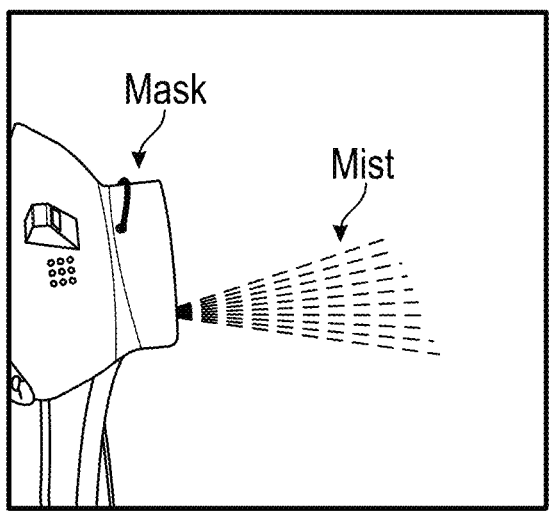
Figure 18E:
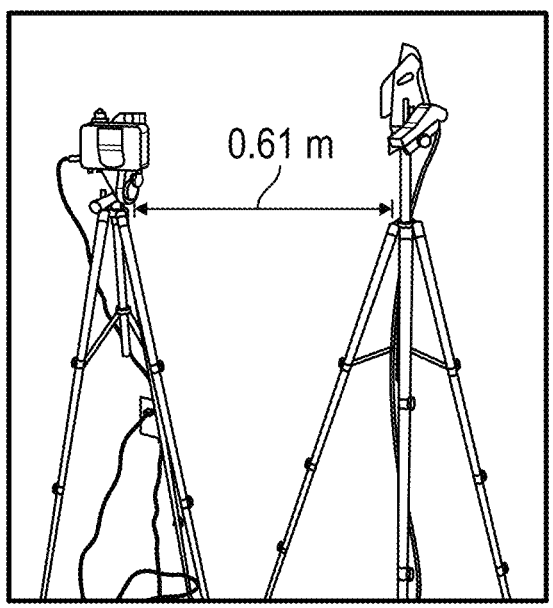
Figure 18F:
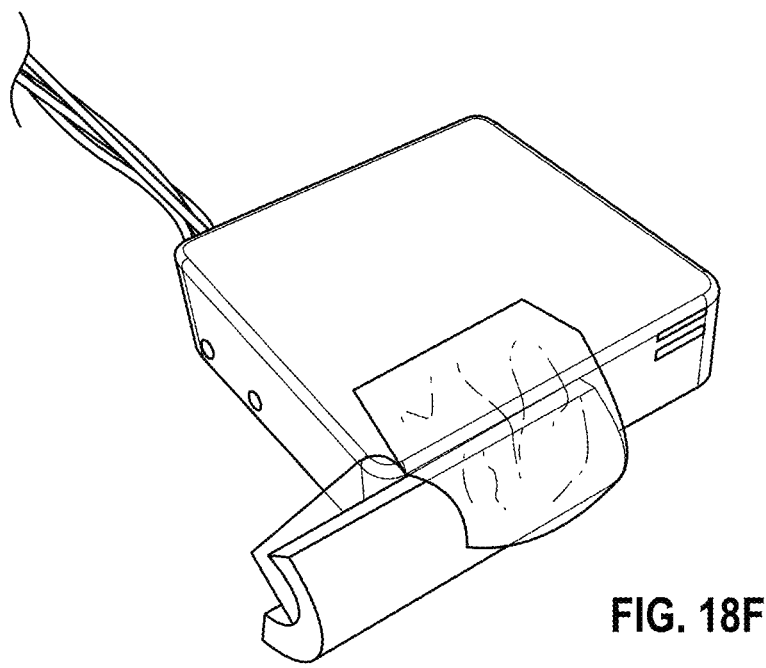
Figure 18G:
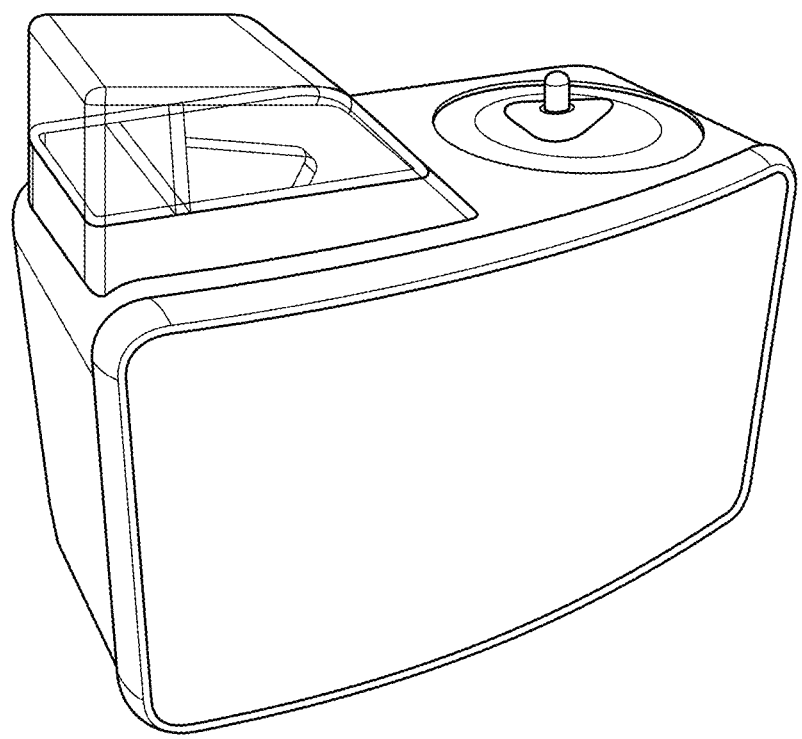

Further, FIGS. 18A-18H illustrates various components of another embodiment of a mask apparatus 1800. FIG. 18A illustrates a front view of the mask apparatus 1800. FIG. 18B illustrates a side view of the mask apparatus 1800 from FIG. 18A. FIG. 18A and FIG. 18B include various dimensions for the mask apparatus 1800. FIG. 18C illustrates a perspective view of the mask apparatus that includes a mask and a belt unit. FIG. 18D illustrates the mask apparatus 1800 generating mist from a port in the mask. FIG. 18E displays an experimental setup showing a mask and the humidifier. FIG. 18F illustrates a PM sensor (sized 41.2 mm×41.2 mm) used in the experiments. FIG. 18G displays a humidifier used to mimic aerosols produced from human activity. FIG. 18H illustrates graphs of a data being collected from the mask apparatus 1800, processed and visualized on a mobile application.

The smart mask apparatus 1800 can include a wearable mask 1801, a liquid reserve compartment 1805, a spray assembly 1808, transducer, a sensor, and other suitable components. The smart mask apparatus 1800 integrates a sensing module 103 (FIG. 1), that senses the presence of airborne aerosol droplets (typical diameter 0.1-10 mm) in the vicinity of the users respiratory tract. The smart mask apparatus 1800 can intake air and can use a sensor to determine the size of the air particles. It incorporates an optical detector system and auxiliary humidity and temperature sensors (as described previously) to quantify the total number and size distribution of these droplets as they approach the protected region (i.e., the nose and mouth). The outputs of both sensors are processed by an air quality analyzer module. The latter uses algorithms to analyze sensor data and thereby classify the quality of the incoming air stream based on health risk (e.g., "very high," "high," "moderate," and "low"). These risk categories are then encrypted for security and sent to the mitigation module either wirelessly (e.g., over Bluetooth) or by using a wired connection. A "high risk" output triggers the active protection mechanism, as summarized in FIG. 18B. The protection mechanism sprays a mist that is safe for human exposure by using a micro nozzle. This module is triggered by an electromechanical relay driven by the system controller.

The hardware and software required for both sensing and mitigation modules are implemented using low-cost commercial off-the-shelf components (a low-power microcontroller and a wireless system-on-module) built within a mask, thus enabling widespread deployment in the vulnerable population. Furthermore, the device can be equipped with machine learning algorithms that learn when respiratory droplets are likely to be present in a location and proactively employ the proposed active protection mechanism. The smart mask can also connect to authorized mobile devices through its wireless module. Users can use a mobile application to monitor current air quality, check system status (e.g., battery and liquid levels), and also manually override the on-board mitigation algorithm.

The smart mask apparatus 1800 has two wearable components: the mask and the belt unit. The mask consists of a liquid reserve, transducer, and the sensor. The belt unit consists of a microcontroller, oscillator circuit, relay, and battery. Three-dimensional (3-D) views of our smart mask prototype are shown in FIGS. 18A and 18B, respectively; photographs of the fully assembled version are shown in FIGS. 18C and 18D. Our prototype uses a cable to connect the mask and belt units; later versions can use a wireless link to avoid the cable.

The experimental setup for testing the functional prototype uses a humidifier to replicate aerosol-sized droplets generated during daily activities like talking, coughing, and sneezing. The humidifier (see FIG. 3G) produces mist droplets in the 0.3-2.5 mm range. Since standard face masks filter out most large droplets (as mentioned earlier), the smart mask's performance was checked against droplets of size <0:3 mm. Two PM sensors (Sensirion SPS30, see FIG. 18F were used: one on the smart mask (which is placed at a height of ~1.6 m), and the other on the ground (see FIG. 18E). The types of sensors can vary. The use of two sensors allows us to quantify both predicted effects of PM loading by the mitigation spray: i) reduction in PM count near the mask, and ii) increase in PM count on the ground (due to the rapid falling of loaded particles). Note that the PM sensor on the ground is not part of the mask, and only used during testing. The chosen PM sensor is based on laser scattering and has built-in "contamination resistance" feature in which artificial air flow (created using a small built-in fan) is used to drive deposited particles out of the sensor. Due to the placement of the exhaust vent, this air flow interferes with the incoming air. To reduce this effect, a guided path was provided for the exhaust as shown in FIG. 18F. In some embodiments, the guided path/vent is not connected to anything. It can outlet the analyzed air into the environment. The shape of the vent can be chosen to be cylindrical to provide for smoother air passage.

The spray assembly 1808, which is a component of the mitigation module 106, includes vary components for generating a spray or mist as a mitigation tool for a detect airborne pathogen. The spray assembly 1808 can include a spray port, a piezo-electric transducer, and other suitable components. The piezo-electric transducer can vibrate at a frequency of 110 kHz. The vibrating portion of the transducer is a mesh-like structure with one side facing the liquid and the other side facing the atmosphere. The pressure drop created by the vibration converts liquid water into vapor, which exits the transducer as shown in FIG. 18D. The transducer runs at 5 V while consuming up to 0.3 A of current. Power is provided by a single 2200 mAh Li-polymer cell. At full load the system consumes 0.4 A. Assuming i) the transistor switches ON for 30 s every time it detects the particles, and ii) 100 such detection events per day, a battery life of ~6 days is expected. A microcontroller handles transmission of the data to the mobile app and responds to control signals from the mobile app. The mobile app processes and visualizes the data for the end user FIG. 18H.

All experiments were conducted in a well-controlled indoor environment with no nearby air vents; this is because aerosols are very sensitive to weak air flows (e.g., due to air-conditioning). Initially, the outputs of the two sensors were checked to ensure a stable and uniform PM concentration in the area around the experimental setup. Next, wo calibration experiments were performed. First, the humidifier was turned ON, which imitates droplets produced by human actions, for 15 s with the mitigation module turned OFF. The aerosols were then allowed to settle for 160 s, with both PM sensors recording their local number and mass concentrations. Second, the same experiment was repeated, but with the smart mask's mitigation module turned ON under normal conditions, i.e., with the humidifier turned OFF. Finally, the effectiveness of the smart mask was verified, as follows. The humidifier was turned ON for 15 s, and the smart mask activated for 15 s once its sensor detects a significant local change in PM concentration. The outputs of both PM sensors were then monitored until all aero-sols settle out (~160 s). The experimental results are analyzed in the next section.

Figures 19A, 19B, 19C:
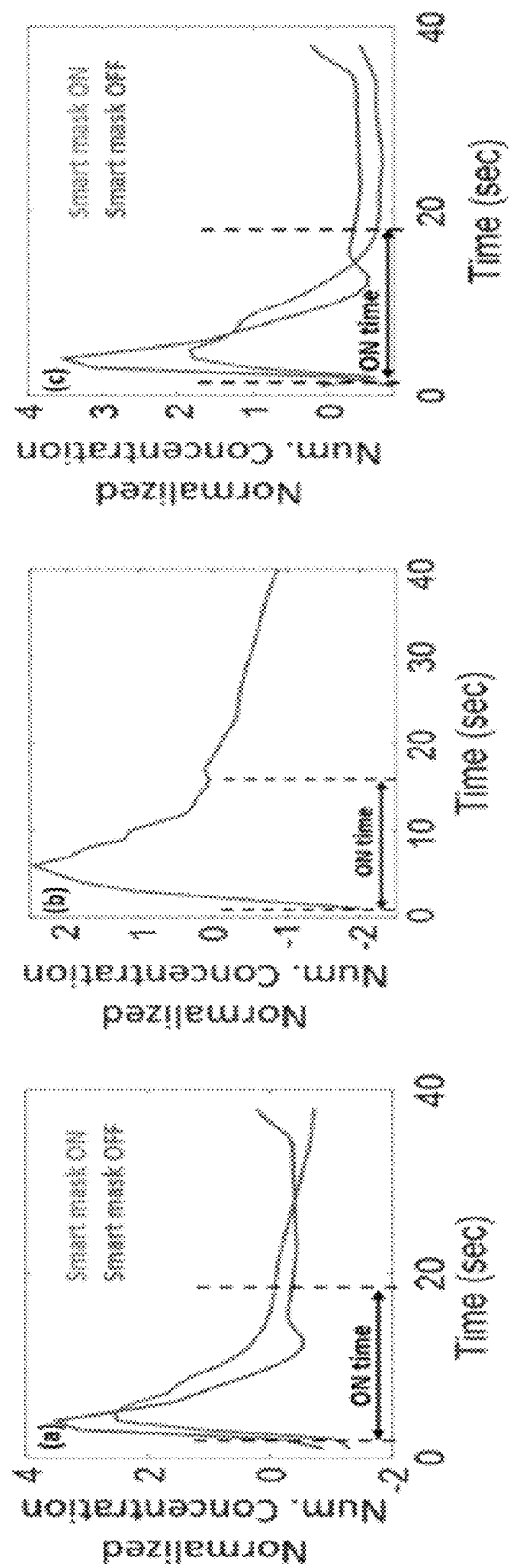
FIGS. 19A-19F illustrates various graphs data collected by a particulate matter sensor, according to one embodiment described herein.
Figure 19F:
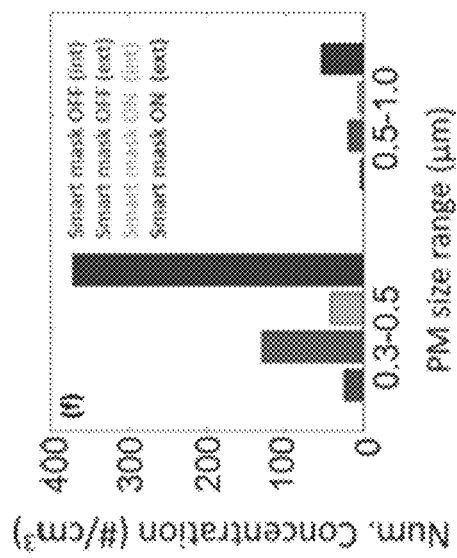
Figure 19E:
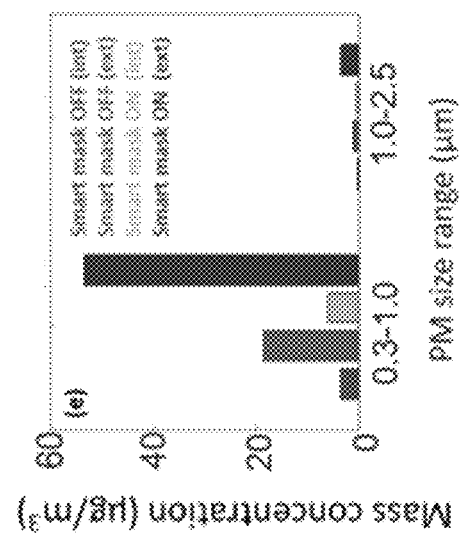
Figure 19D:
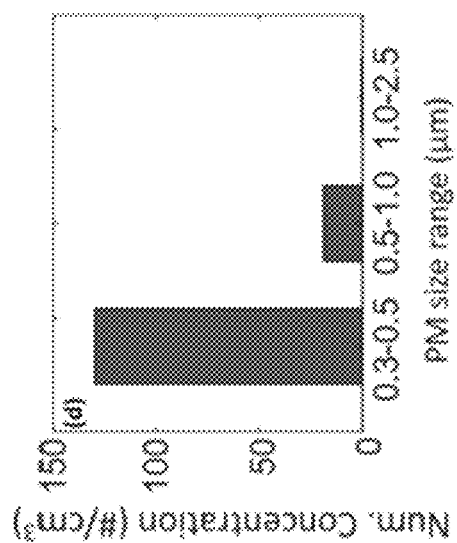

FIG. 19A shows PM number concentration detected by the sensor on the smart mask, with only the size range of interest (0.3-1.0 mm) considered, in two cases: mitigation module ON and OFF. Clearly, the mitigation module (e.g., mist generator) significantly reduces the local PM number within this critical size range—simple analysis suggests a time-averaged reduction of □20%. Moreover, the PM count with the mitigation module ON is artificially increased due to the aerosols generated by the module itself [see FIG. 4(b)]. Once this self-interference term is subtracted, the time-averaged reduction in PM count due to the mask becomes even more significant—FIG. 18C suggests ~40%.

The aerosol concentrations produced by the humidifier in the 0.3-2.5 mm range resemble those produced during daily activities, and are shown in FIG. 4(d). Next, the effect of the smart mask were analyzed on the concentration of these aerosolized particles. FIGS. 4(e) and (f) com-pares the time-averaged mass and number concentrations with the mask ON and OFF for both internal (on the mask) and external (on the ground) PM sensors. The data shows that the mass concentrations measured by the external sensor in the 0.3-1.0 mm and 1.0-2.5 mm ranges increase by ~63% and ~60%, respectively, when the mask is turned ON. Similarly, the corresponding number concentrations increase by ~62% and ~50%, respectively. These results suggest that the smart mask loads the local aerosol particles as expected, causing them to fall faster to the ground.

The mechanical structure of the mask 1801 can be built from an open-source 3-D design. The mechanical structure was designed to include a first compartment 1805 for a liquid storage and a second compartment 1806 for sensor components (see FIGS. 18A and 18B). The mask 1801 includes an outer perimeter area that curves toward the center. In some embodiments, the first compartment 1805 is substantially at the center of the mask 1801. As such, the first compartment 1805 extends laterally away from the outer area of the mask, and the first compartment 1805 has a front wall that includes an exit port for the spray assembly 1808. The transducer is placed flush with the mask's inner surface, with one of its sides facing the liquid. In some embodiments, one or more sensors (e.g., PM sensors, LIDAR sensors, temperature sensors, humidity sensors) can be located in the second compartment 1806 in FIG. 18A. Small perforations backed by replaceable air filters are added on the sides of the mask to ensure adequate air intake. Additionally, the edges 1809 can be lined with silicone, thus ensuring a good seal with the skin. The second compartment on the mask holds the sensor, while a small pocket- or belt-worn external unit houses the battery and system controller. The mask with the sensor on board weighs 110 g without liquid reserve, while the belt unit weighs another 120 g. The mask was 3-D-printed for testing purposes, but can instead be injection-molded to reduce cost, weight and thickness for mass production. In that case, the overall manufacturing cost per mask (including the electronics) is expected to be about $25.

The various embodiments relate to a novel method of a system and method for closed-loop active protection against airborne pathogens and allergens, including viruses, such as novel coronavirus, flu, pollen, etc. For example, some of the improvements can include a system and method for closed-loop active protection against airborne pathogens and allergens, including viruses such as the novel coronavirus, flu, measles, etc. The embodiments can sense environmental parameters to detect the existence of potentially virus-laden respiratory droplets floating in the air (originating from infected people) and based on the sensed parameters, take immediate action to kill the pathogen.

Additionally, the embodiments can include a sensing device or sensing device. Some embodiments can include a closed-loop system that can continuously sense the presence of respiratory droplets (typically 0.1μm-10 μm diameter) in the immediate environment of the respiratory tract. It can integrate an optical detector, various auxiliary sensors, and a trained machine learning (ML) algorithm to quantify the sizes, pathogens, and concentration of these droplets as they approach the protected surface (the nose and mouth). The sensor module 103 can optionally integrate an additional airflow sensor further to quantify the rate of flow of respiratory droplets.

In addition, the embodiments can include active protection system or module. The embodiments can integrate an active protection mechanism triggered by the sensing device. The active protection mechanism can be based on at least one of two approaches. First, the active protection mechanism can spray a disinfectant that is safe to human exposure by using a miniature electromagnetic nozzle and a flexible chamber. For example, if the proposed system is put on a mask, the chamber can be a flexible bag that can wrap around the mask surface. Alternatively, it can be integrated within the headgear (the active hat concept). Second, the active protection mechanism can direct pulses of UV-C light generated using an array of UV light-emitting diodes (LEDs).

In addition, the embodiments can include at least one of two possible embodiments of the system/method, but many other embodiments are possible. Some embodiments can include: (a) a smart mask, in which both the sensing and the active mitigation modules are integrated within a face mask; and (b) an active hat, in which both the modules are placed on headgear (a hat or cap). Alternative arrangements, e.g., placing the sensor module 103 in the mask and the active mitigation module on the hat, are also possible. Also, the placement of such a closed-loop system in strategic places on a vulnerable surface, where the virus-laden droplets land, is possible and can be highly beneficial.

In addition, the embodiments can be equipped with a machine learning (ML) algorithm that can learn when such respiratory droplets are likely to be present in a location and proactively employ the proposed active protection mechanism. From spectrography, unique signatures of various pathogens can be determined, and from the collected data, the signature of the various pathogen can be classified in real-time using boundary scan and can provide necessary mitigation methods.

In addition, user locations can be tracked precisely with the use of Wi-Fi access points and GPS in places such as hospitals, commercial buildings, and other suitable facilities. This allows for the embodiments to provide automatic protection against airborne pathogens by using mitigation methods like disinfectant spray or by using UVC through our ADAPT stationary systems at potentially vulnerable locations.

Further, the embodiments can be used to mitigate against allergens and other harmful airborne droplets because most viruses are airborne with water molecules and the aerosol size of pathogens is comparable to the size of pollen. As most people do not wear masks for allergens, and as ADAPT system 100 is patchable they can use smart helmets to prevent contact with allergens.

Additionally, the ADAPT system 100 also has a manual override option which allows the user to take control of the system in scenarios where human intervention should be prioritized. Further, the sensor inputs and the controller of the ADAPT system 100 can be connected to a cell phone through the wireless module. A wearer can monitor the status of the amount of remaining liquid from the cell phone, as well as allow the wearer to override the mitigation step, such as the ejection of the cold mist or compressed gas or disinfectant. The ADAPT system 100 can send an alert in a user's cell phone when it needs to be refilled.

Additionally, the embodiments of ADAPT system can also be equipped with additional chemical sensors (e.g., electrochemical detectors) to determine the level of active protective agents present in aerosol droplets. This information can be used to i) warn users, and ii) control the release of disinfectant from the smart mask. Similarly, it can also be used to detect and protect users from Biotoxins.

Various embodiments for a system and method for closed-loop active protection against air-borne pathogens and allergens, including viruses such as the novel coronavirus, flu, etc., have been described. The embodiments can sense environmental parameters to detect the existence of potentially virus-laden respiratory droplets floating in the air and takes immediate action to kill the pathogen in real-time. It can be integrated into smart wearable devices (smart masks and hats), each of which contains two hardware modules that interact with each other. The sensor module 103 can detect airborne pathogens. The protection/mitigation module 106 can use a safe mitigation method (disinfectant spray or UV-C radiation) to eradicate them. The present disclosure has described various prototypes of some of the embodiments in detail, and also provided brief predictions of the potential for many other embodiments.

The embodiments can be useful for professionals and ordinary citizens alike, but for different purposes. In particular, it can help first responders and medical workers by making their work environment safer. Also, it can allow regular people to continue their daily activities without fear of being affected by an ongoing infectious disease outbreak.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The invention claimed is:

1. A wearable apparatus for an individual, comprising:
   a sensor device that comprises an aerosol detector, a first auxiliary sensor, and a second auxiliary sensor, the aerosol detector being configured to perform a light measurement of an airborne aerosol droplet in an area proximate to the wearable apparatus, the first auxiliary sensor and the second auxiliary sensor measure different sensory elements;
   a mitigator device that is configured to initiate a mitigation action directed at the airborne aerosol droplet;
   a controller that is in data communication with the sensor device and the mitigator device, wherein the controller is configured to at least:
   determine that the airborne aerosol droplet has a pathogen based at least in part on the light measurement captured by the sensor device at a first time period;
   cause the mitigator device to initiate the mitigation action based at least in part on the determination of the airborne aerosol droplet having the pathogen;
   determine a first rate of change for a first sensor measurement of the first auxiliary sensor and a second rate of change for a second sensor measurement of the second auxiliary sensor at a second time period; and cause the mitigator device to terminate the mitigation action based at least in part on the first rate of change and the second rate of change satisfying a constant value of a function, wherein the function is associated with reducing a dampening oscillation a rate of change of a sensor measurement from the sensor device at a second time period that is after the first time period.

2. The apparatus of claim 1, wherein the aerosol detector comprises a laser-inducted fluorescence detector (LIDAR).

3. The apparatus of claim 1, wherein the first rate of change of the first sensor measurement is a temperature rate of change of a temperature measurement received from the first auxiliary sensor of the sensor device, wherein the temperature measurement is associated with the airborne aerosol droplet.

4. The apparatus of claim 1, wherein the second rate of change of the second sensor measurement is a humidity rate of change of a humidity measurement received from the second auxiliary sensor of the sensor device, wherein the humidity measurement is associated with the airborne aerosol droplet.

5. The apparatus of claim 1, wherein determining that the airborne aerosol droplet has the pathogen is further based at least in part on a machine learning classification model, wherein the machine learning classification model is provided input from at least one sensor of the sensor device.

6. The apparatus of claim 5, wherein the input provided to the machine learning classification model comprises at least one of an aerosol droplet size, a temperature of the airborne aerosol droplet, and a concentration of the airborne aerosol droplet.

7. The apparatus of claim 1, wherein the mitigation action comprises at least one of: releasing a compressed gas directed at the airborne aerosol droplet, spraying cold water mist, spraying a disinfectant solution directed at the airborne aerosol droplet, or emitting an ultraviolet light directed at the airborne aerosol droplet.

8. The apparatus of claim 7, further comprising a spray nozzle, and wherein releasing the compressed gas directed at the airborne aerosol droplet further comprises releasing a disinfectant or cold-water mist, directed at the airborne aerosol droplet and/or to control an air flow pattern around the wearable apparatus.

9. The apparatus of claim 8, wherein the compressed gas is directed at the airborne aerosol droplet based at least in part on measuring at least one of a location of the airborne aerosol droplet, a spatial span, and a quantity of the airborne aerosol droplets.

10. A method comprising:
receiving, via a controller, a light measurement of an airborne aerosol droplet from an aerosol detector;
determining, via the controller, that the airborne aerosol droplet has a pathogen based at least in part on the light measurement at a first time period;
causing, via the controller, a mitigation device to initiate a mitigation action directed at the airborne aerosol droplet based at least in part on the determination of the airborne aerosol droplet having the pathogen;
determining, via the controller, a first rate of change for a first sensor measurement of a first auxiliary sensor and a second rate of change for a second sensor measurement of a second auxiliary sensor at a second time period; and cause the mitigator device to terminate the mitigation action based least in part on the first rate of change and the second rate of change satisfying a constant value of a function.

11. The method of claim 10, wherein the aerosol detector comprises a laser-inducted fluorescence detector (LIDAR).

12. The method of claim 10, further comprising:
determining, via the controller, that a quantity of the pathogen exceeds a quantity threshold based at least in part on a quantity measurement of the pathogen in the airborne aerosol droplet.

13. The method of claim 10, wherein determining that the airborne aerosol droplet has the pathogen is further based at least in part on a temperature measurement received from the first auxiliary sensor, wherein the temperature measurement is associated with the airborne aerosol droplet.

14. The method of claim 10, wherein determining that the airborne aerosol droplet has the pathogen is further based at least in part on a humidity measurement received from the second auxiliary sensor, wherein the humidity measurement is associated with the airborne aerosol droplet.

15. The method of claim 10, wherein determining that the airborne aerosol droplet has the pathogen is further based at least in part on a machine learning classification model, wherein the machine learning classification model is provided input from the aerosol detector.

16. A mask system, comprising:
a mask configured to be worn over a face of an individual;
a sensor device that comprises an aerosol detector, a first auxiliary sensor, and a second auxiliary sensor, the aerosol detector being that is configured to perform a measurement of an airborne aerosol droplet in an area proximate to the mask;
a mitigator device that is configured to initiate a mitigation action directed at the airborne aerosol droplet;
a controller that is in data communication with the sensor device and the mitigator device, wherein the controller is configured to at least:
determine that the airborne aerosol droplet has a pathogen based at least in part on the measurement captured by the sensor device at a first time period;
cause the mitigator device to initiate the mitigation action based at least in part on the determination of the airborne aerosol droplet having the pathogen;
determine a first rate of change for the first auxiliary sensor and a second rate of change for the second auxiliary sensor at a second time period; and
cause the mitigator device to terminate the mitigation action based least in part on the first rate of change and the second rate of change satisfying a constant value of a function.

17. The mask system of claim 16, wherein the aerosol detector comprises at least one of a laser-induced fluorescence detector, or an asymmetric microsphere resonant detector.

18. The mask system of claim 16, wherein the mask comprises a first compartment that comprises the sensor device, and a second compartment that comprises a liquid reserve of a disinfectant solution.

19. The mask system of claim 18, further comprising:
a transducer; and
wherein the mitigation action comprises the mitigator device using the transducer to access the liquid reserve in order to generate a vapor of the disinfectant solution.

20. The mask system of claim 16, wherein the function is an error function.

* * * * *